US007427504B2

(12) United States Patent
Torgersen et al.

(10) Patent No.: US 7,427,504 B2
(45) Date of Patent: Sep. 23, 2008

(54) DETERMINING FLUID CHEMISTRY OF FORMATION FLUID BY DOWNHOLE REAGENT INJECTION SPECTRAL ANALYSIS

(75) Inventors: Torleif Torgersen, Soereidgrend (NO); Bhavani Raghuraman, Wilton, CT (US); Edward Harrigan, Richmond, TX (US); Oliver C. Mullins, Ridgefield, CT (US); Gale Gustavson, Brookfield, CT (US); Philip Rabbito, Milford, CT (US); Ricardo Reves Vasques, Sugar Land, TX (US)

(73) Assignee: Schlumber Technology Corporation, Ridgefield, CT (US)

( * ) Notice: Subject to any disclaimer, the term of this patent is extended or adjusted under 35 U.S.C. 154(b) by 712 days.

(21) Appl. No.: 10/667,639

(22) Filed: Sep. 22, 2003

(65) Prior Publication Data

US 2004/0129874 A1    Jul. 8, 2004

(51) Int. Cl.
*G01N 33/24* (2006.01)
*G01N 21/00* (2006.01)
*G01N 21/75* (2006.01)
*G01N 21/03* (2006.01)

(52) U.S. Cl. .................. 436/28; 436/164; 436/165; 436/166

(58) Field of Classification Search .......... None
See application file for complete search history.

(56) References Cited

U.S. PATENT DOCUMENTS 5,246,862 A * 9/1993 Grey et al. .................. 436/28

| | | | | |
|---|---|---|---|---|
| 5,597,042 A | * | 1/1997 | Tubel et al. ............. | 166/250.01 |
| 5,783,740 A | * | 7/1998 | Tawarayama et al. ........ | 73/19.1 |
| 6,058,773 A | | 5/2000 | Zimmerman et al. ..... | 73/152.24 |

(Continued)

FOREIGN PATENT DOCUMENTS

| EP | 0461321 B1 | 12/1991 |
|---|---|---|
| GB | 2362462 A | 11/2001 |
| WO | 99/00575 A3 | 1/1999 |
| WO | 01/73424 A1 | 10/2001 |

(Continued)

OTHER PUBLICATIONS

Andrews, R. J. et al. *Quantifying Contamination Using Color of Crude and Condensate.* Oilfield Review, pp. 24-43 (2001).

(Continued)

*Primary Examiner*—Yelena G Gakh
(74) *Attorney, Agent, or Firm*—James McAleenan, Esq.; Vincent Loccisano, Esq.; Jody Lynn DeStefanis, Esq.

(57) ABSTRACT

A method for analyzing formation fluid in earth formation surrounding a borehole includes storing analytical reagent in a reagent container in a fluids analyzer in a formation tester and moving the formation tester, including the reagent, downhole. Reagent from the reagent container is injected into formation fluid in the flow-line to make a mixture of formation fluid and reagent. The mixture is moved through a spectral analyzer cell in the fluids analyzer to produce a time-series of optical density measurements at a plurality of wavelengths. A characteristic of formation fluid is determined by spectral analysis of the time-series of optical density measurements.

23 Claims, 20 Drawing Sheets

U.S. PATENT DOCUMENTS 6,176,323 B1 * 1/2001 Weirich et al. ................ 175/40
6,564,866 B2 * 5/2003 Clark et al. ............ 166/250.12
6,588,266 B2 * 7/2003 Tubel et al. .............. 73/152.39

OTHER PUBLICATIONS

Bates, R. G. *Determination of pH: Theory and Practice.* Chapter 6, pp. 131-165 (1964).

Ruzicka, J. et al. *Flow Injection Analysis.* Chapter 1, pp. 1-9 (1981).

Vogel, A. I. *A Text-Book of Quantitative Inorganic Analysis.* 3rd Ed., Chapters 10-12, pp. 782-853 (1961).

Ayan et al., "Characterizing Permeability With Formation Testers", Oilfield Review—Autumn 2001, vol. 13, No. 3.

* cited by examiner

DETERMINING FLUID CHEMISTRY OF FORMATION FLUID BY DOWNHOLE REAGENT INJECTION SPECTRAL ANALYSIS

This application claims priority to co-owned, co-pending GB patent application no. 0227267.2, to Raghuraman et al., "Apparatus and Method for Analysing Downhole Water Chemistry", filed 22 Nov. 2002.

FIELD OF THE INVENTION

The invention is intended for use in the petroleum industry, or in any industry requiring the characterization of fluids residing downhole in a fluid reservoir in an earth formation surrounding a borehole.

BACKGROUND OF THE INVENTION

In oil well evaluation, quantitative analyses of formation fluid are typically performed in a laboratory environment, the samples having been collected downhole and brought to the surface in the sample chamber of a wireline formation tester.

Standard laboratory procedures are available to do quantitative analyses by addition of a reagent that reacts chemically with a specific target species in a sample to cause detectible changes in fluid property such as color, absorption spectra, turbidity etc. See Vogel, A. I., "Text-Book of Quantitative Inorganic Analysis, 3rd Edition", Chapter 10-12, John Wiley, 1961. Such changes in fluid property may be caused, for example, by the formation of a product that absorbs light at a certain wavelength, or by the formation of an insoluble product that causes turbidity, or bubbles out as gas. For example, addition of pH sensitive dyes is used for calorimetric pH determination of water samples. A standard procedure for barium determination requires addition of sodium sulfate reagent to the fluid sample resulting in a sulfate precipitate that can be detected through turbidity measurements. Some of these standard laboratory procedures have been adapted for flow injection analysis (Ruzicka, J. and Hansen, E. H., Flow Injection Analysis, Chapters 1 and 2, John Wiley, 1981). Flow injection analysis "is based on the injection of a liquid sample into a moving non-segmented continuous carrier stream of a suitable liquid" (Chapter 2, page 6).

Fluid samples collected downhole can undergo various reversible and irreversible phase transitions between the point of collection and the point of analysis as pressure and temperature conditions are hard to preserve. Concentrations of constitutive species may change because of loss due to vaporization, precipitation etc., and hence the analysis as done in the laboratories may not be representative of true conditions downhole. For example, water chemistry and pH are important for estimating scaling tendencies and corrosion; however, the pH can change substantially as the fluid flows to the surface. Scaling out of salts and loss of carbon dioxide and hydrogen sulfide can give misleading pH values when laboratory measurements are made on downhole-collected samples.

While downhole formation sampling tools are usually equipped with spectrophotometric detectors, currently there are no available methods to carry one or more reagents downhole and inject them into the flow-line to enable such an analysis.

SUMMARY OF THE INVENTION

A method for analyzing formation fluid in earth formation surrounding a borehole includes storing analytical reagent in a reagent container in a fluids analyzer in a formation tester and moving the formation tester, including the reagent, downhole. Reagent from the reagent container is injected into formation fluid in the flow-line to make a mixture of formation fluid and reagent. The mixture is moved through a spectral analyzer cell in the fluids analyzer to produce a time-series of optical density measurements at a plurality of wavelengths. A characteristic of formation fluid is determined by spectral analysis of the time-series of optical density measurements.

A method for determining fluid chemistry of formation fluid in earth formation surrounding a borehole includes storing analytical reagent in a reagent container coupled to a fluids analyzer via a flow-line in a formation tester, transporting the formation tester downhole, drawing formation fluid into the flow-line, moving a mixture of formation fluid and analytical reagent through a spectral analyzer cell in the fluids analyzer, and performing reagent injection spectral analysis on the mixture. Performing reagent injection spectral analysis includes injecting reagent into the flow-line to create a mixture of formation fluid and reagent in the flow-line. Preferably, the method further includes establishing and storing baseline optical density values for at least one wavelength prior to injecting reagent. Preferably, injecting reagent includes injecting a predetermined volume of reagent into formation fluid within the flow-line. Preferably, injecting reagent includes adjusting the predetermined volume. Preferably, adjusting the predetermined volume includes adjusting an injection period of time. Preferably, injecting reagent includes injecting reagent into a stopped formation fluid. Preferably, injecting reagent includes injecting reagent using a syringe pump.

Alternatively, adjusting the predetermined volume includes adjusting an injection pump rate.

Alternatively, injecting reagent includes injecting reagent into a flowing formation fluid.

Alternatively, injecting reagent includes injecting reagent using wellbore overpressure using a restrictor or a throttle valve.

Alternatively, injecting reagent includes extracting formation fluid from a stopped flow-line using a syringe pump, a flow-line pump, or a step piston.

A fluids analyzer for analyzing formation fluid in earth formation surrounding a borehole includes a probe for receiving downhole formation fluid from earth formation, a flow-line coupled to receive formation fluid downhole from the probe, a reagent container in fluid communication with the flow-line, spectral analyzer means coupled to receive a mixture of formation fluid and reagent from the flow-line downhole for analyzing the mixture to produce time-series optical density data at a plurality of wavelengths, and computing means for determining a characteristic of formation fluid from the optical density data. Preferably, the reagent container is a syringe pump.

Alternatively, the reagent container is exposed to wellbore pressure. Alternatively, a fluid container is coupled to extract fluid from the flow-line.

Optionally, a second reagent container is provided in communication with the flow-line independently of a first reagent container.

DETAILED DESCRIPTION

General

The present invention provides a method and apparatus for determining fluid chemistry of formation fluid in an earth formation surrounding a borehole. In particular, it provides a novel method and apparatus for delivering a suitable mixture of formation fluid and analytical reagent to a downhole spectral analyzer.

The above-mentioned priority document, patent application GB 0227267.2 discloses a method for analyzing downhole water chemistry. It discloses a general approach to analysis of water chemistry including details of the chemistry and the spectral analysis involved. This approach requires injecting a specific indicator or reagent into a sample of water and determining the resulting color of the fluid with an optical spectrophotometer. Patent application GB 0227267.2 is hereby incorporated herein by reference.

The present invention, in a preferred embodiment, also requires injecting reagent into a downhole sample of formation fluid, and discloses an apparatus and a method to do this. The present invention also discloses in detail a novel method for injecting reagent into formation fluid that may contain any of water, oil, and gas, to make a suitable mixture of formation fluid and analytical reagent for downhole spectral analysis. The method includes transporting reagent downhole, inserting or drawing analytical reagent into formation fluid to make a mixture of formation fluid and analytical reagent, and advancing the mixture through the cell of a spectral analyzer for downhole spectral analysis. A preferred embodiment uses a reagent container and an injector pump (syringe injector pump) for injecting reagent into the flow-line. Other embodiments use well bore overpressure to inject reagent into the flow-line with a restrictor or a throttle valve to control flow rate. This eliminates the need for an injector pump. Other embodiments use a fluid container with a syringe pump, a flow-line pump, or a step piston, to extract formation fluid from the flow-line, thereby inducing reagent injection into the flow-line.

As noted above, flow injection analysis is based on the injection of a liquid sample into a moving non-segmented continuous carrier stream of a suitable liquid. In contrast, the present invention involves downhole injection of reagent into a formation fluid sample.

First Preferred Embodiment

Reagent-Injected-by-Syringe-Pump, Sample-Stopped Mode

FIGS. 1-5 illustrate a first preferred embodiment of the invention configured for reagent injection spectral analysis operating in reagent-injected-by-syringe-pump, sample-stopped mode.

Figure 1:
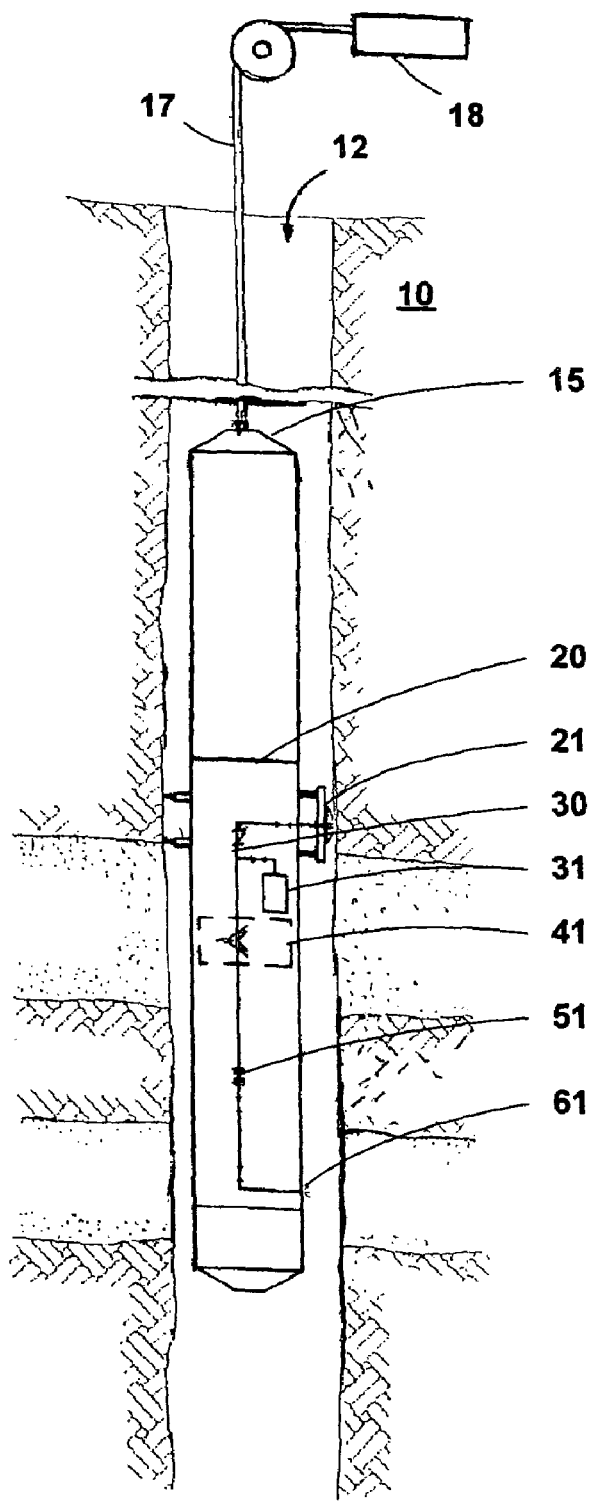
FIG. 1 illustrates a first preferred embodiment of a fluids analyzer of the invention located in a wireline formation tester.

FIG. 1 shows a wireline formation tester 15, including fluids analyzer 20 configured for operation in reagent-injected-by-syringe-pump, sample-stopped mode. The formation tester is shown downhole within borehole 12 of formation 10 suspended by logging cable 17. Logging cable 17 also couples the formation tester to surface system 18. Fluids analyzer 20 is located within formation tester 15. Probe 21 is shown extending from the formation tester. Major elements of fluids analyzer 20 are fluid flow-line 30, reagent container 31, spectral analyzer 41, flow-line pump (dual chamber piston pump) 51, and main pump-out line 61.

Figure 2:
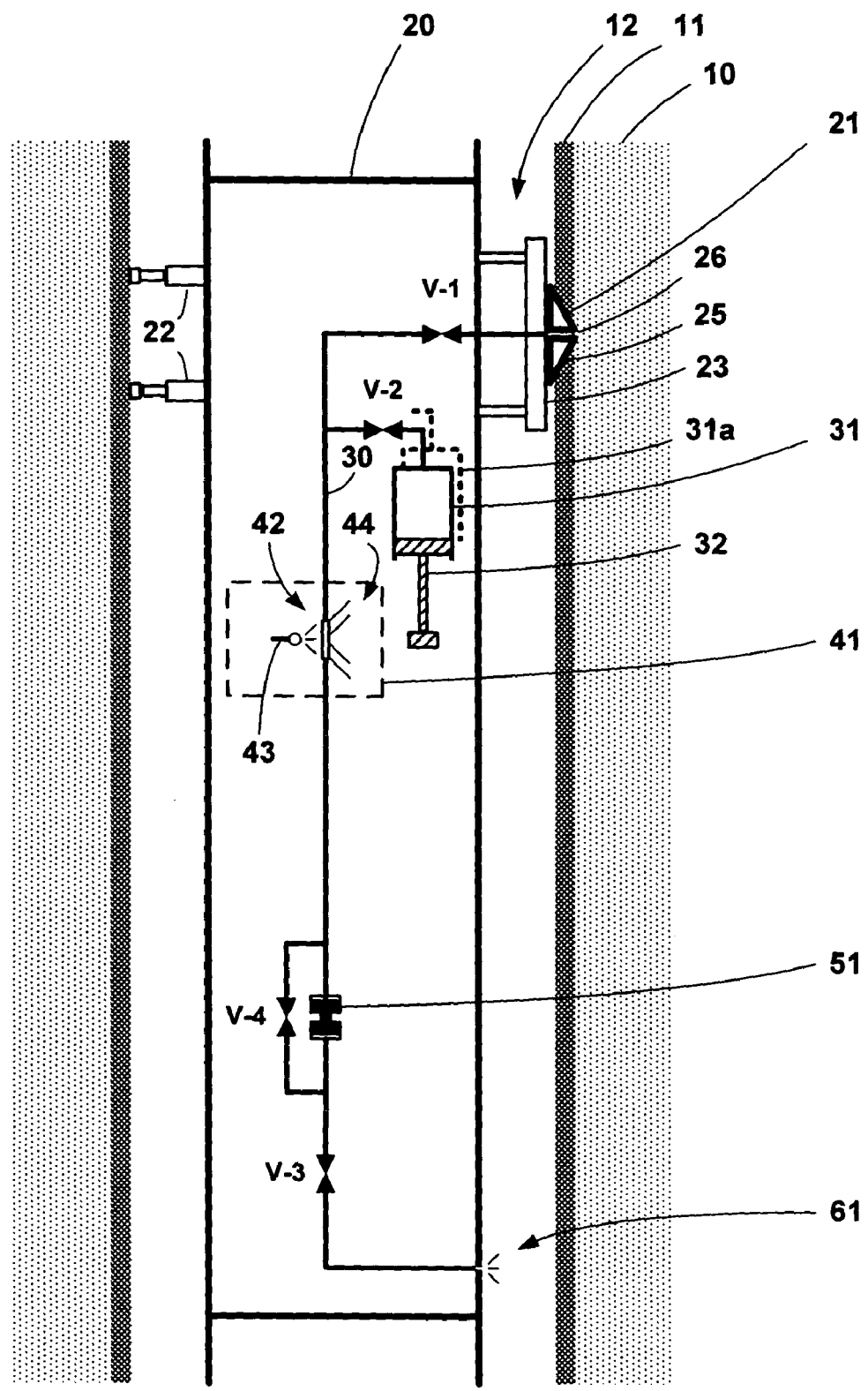
FIG. 2 shows detail of the fluids analyzer of FIG. 1 having an injection syringe pump reagent container, the fluids analyzer configured for executing the steps of a first preferred embodiment of the method.

FIG. 2 shows the formation tester held in position by hydraulic anchoring pistons 22. FIG. 2 also provides more detail of fluids analyzer 20.

Probe 21 is shown mounted to carriage 23 and penetrating mud cake 11. Resilient packer 25 provides a seal and inflow aperture 26 is in fluid communication with formation fluid. Resilient packer 25 seals inflow aperture 26 and flow-line 30 from well bore pressure. (Wellbore pressure is usually greater than formation pressure).

FIGS. 1 and 2 show formation fluid analyzer 20 having probe 21, flow-line 30, reagent container 31 (having an injector pump 32), spectral analyzer 41, and main pump-out line 61. For convenience the probe, the flow-line, and the main pump-out line are shown in a single module. However, typical prior art formation testers include multiple modules sharing a single probe, a single flow-line and a single pump-out line. The present invention is intended to include configurations wherein such elements may be located in different modules but are shared by two or more analyzers.

Flow-line 30 couples aperture 26 to spectral analyzer 41 via first flow-line isolation valve V1. It also provides an entry point for fluid injection of reagent from reagent container 31 via reagent container isolation valve V2. It also couples spectral analyzer 41 to flow-line pump 51, and, via second flow-line isolation valve V3, to main pump-out line 61.

Flow-line 30 has a cross-sectional area of approximately 0.2 cm$^2$.

Reagent container 31 with injector pump 32 in the first preferred embodiment is provided as a syringe injector pump. Preferably, container 31 has a capacity of approximately four liters. The volume of reagent in a single injection is preferably in the range 2-10 cc.

Additional reagent containers, each having its own reagent container isolation valve V2, may be provided to increase reagent storage capacity or to provide the ability to select and inject an alternative reagent without withdrawing the formation tester from the wellbore. An auxiliary reagent container 31a is shown dotted in FIG. 2.

Spectral analyzer 41 is a conventional multi-channel (i.e. multi-wavelength) spectral analyzer, having a spectral analyzer cell 42, an illumination source 43, and an illumination detector 44. Spectral analyzer 41 has at least two channels, preferably more. Measuring pH requires a minimum of two channels. Optical density measurements are made simultaneously on all channels at the rate of at least three per second, preferably higher. To accommodate measurements of a wide range of target measured properties, the spectral analyzer preferably has ten channels, each channel measuring optical density at a different wavelength.

Flow-line pump 51 is a conventional dual-chamber piston pump.

Bypass valve V4 allows excess formation fluid to flow to main pump-out line 61 when reagent is injected into the otherwise stopped flow-line of the first preferred embodiment.

First Preferred Method, Reagent-Injected-by-Syringe-Pump, Sample-Stopped Mode

The first preferred embodiment of the method of the invention uses reagent injection spectral analysis operating in syringe-pumped-injection, sample-stopped mode. The method is summarized in the flowcharts of FIGS. 3-5.

Figure 3:
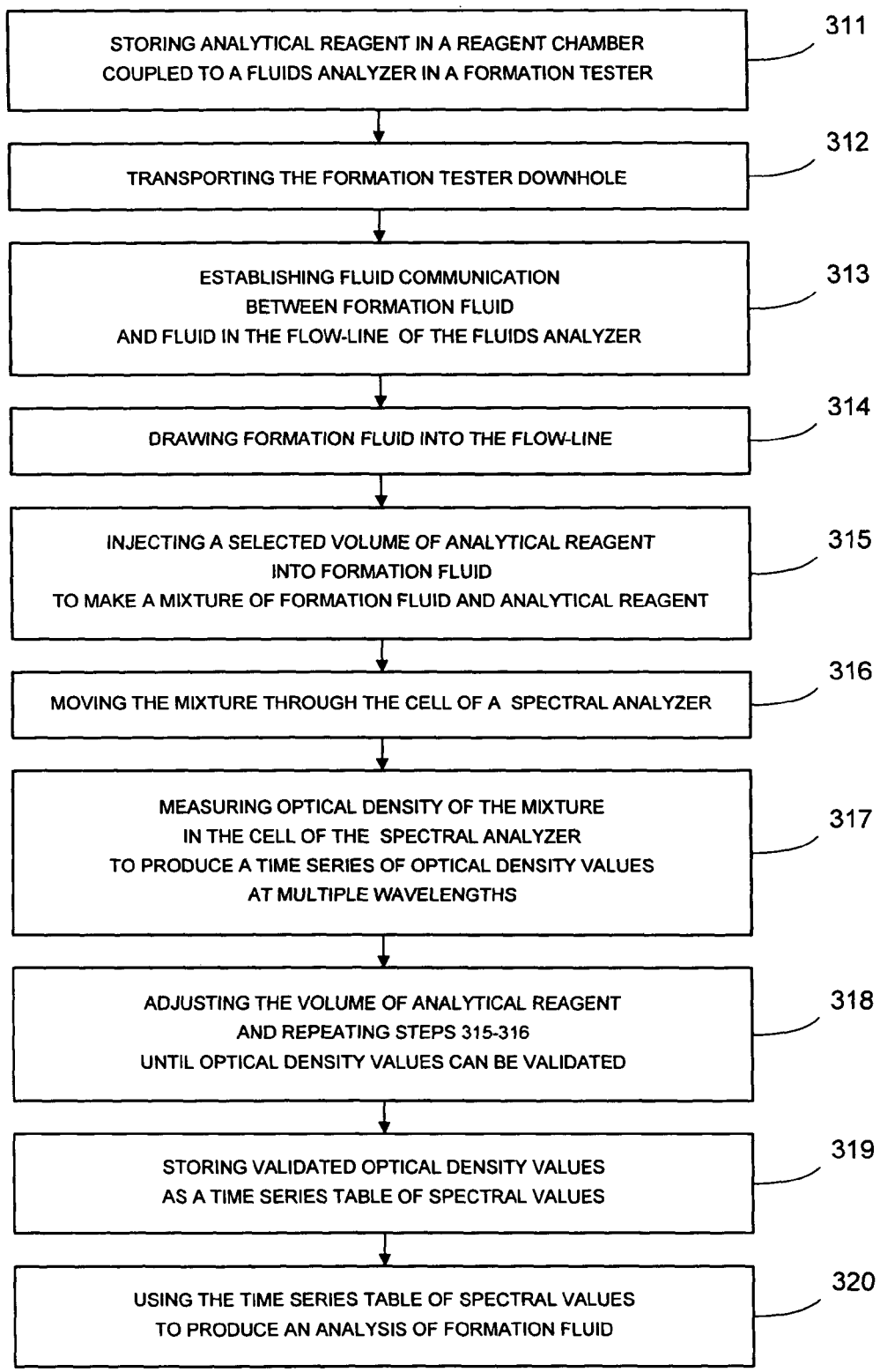
FIGS. 3-5 are flowcharts illustrating the first preferred embodiment of the method of the invention, the method using reagent injection spectral analysis operating in a reagent-injected-by-syringe-pump, sample-stopped mode to determine downhole fluid chemistry.

Referring to FIGS. 2 and 3, reagent container 31 is filled with reagent and formation tester is lowered to a position downhole in the borehole (FIG. 3, 311-312) where it is anchored. Probe 21 is extended such that fluid communication is established (313) between formation fluid and fluid in flow-line 30. Flow-line pump 51 is running, isolation valves V1 and V3 are open, and bypass valve V4 is closed, so formation fluid is drawn (314) via inflow aperture 26 of probe 21 into flow-line 30. The flow rate of formation fluid flowing through the flow-line is preferably in the range 1-20 cc/sec.

Preferably, although not shown in FIG. 3, the method of the invention includes establishing and storing baseline optical density values at multiple wavelengths prior to injection of reagent.

Referring to FIG. 3, a selected volume of analytical reagent is injected (315) into formation fluid in the flow-line to make a mixture of formation fluid and analytical reagent in the flow-line. Because the first preferred embodiment uses the syringe-pumped-injection, sample-stopped mode, it is necessary to open some valves and close other valves before and after injection of reagent. The process of step 315 in FIG. 3 is described in more detail by steps 411-417 of FIG. 4.

Figure 4:
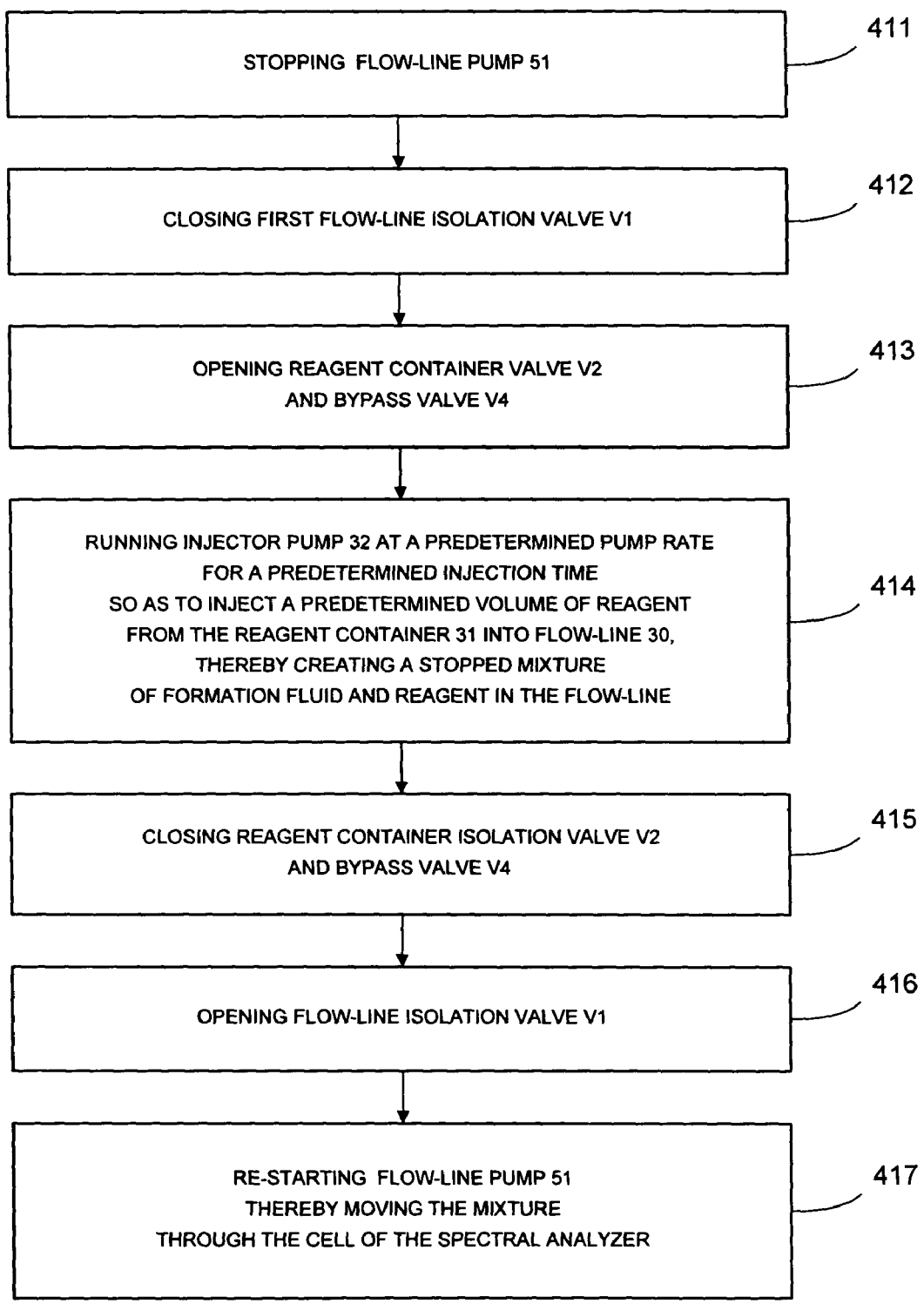

Step 414 of FIG. 4 requires running injector pump 32 at a predetermined pump rate for a predetermined injection time so as to inject a predetermined volume of reagent from the reagent container 31 into flow-line 30. Achieving a suitable volume involves adjusting the volume in accordance with step 318 of FIG. 3, and executing steps 511-513 of FIG. 5 iteratively to provide a suitable value for the volume to inject. These processes are described below. The criteria for "suitable value" can be best understood by reference to FIG. 20A.

Figure 20A:
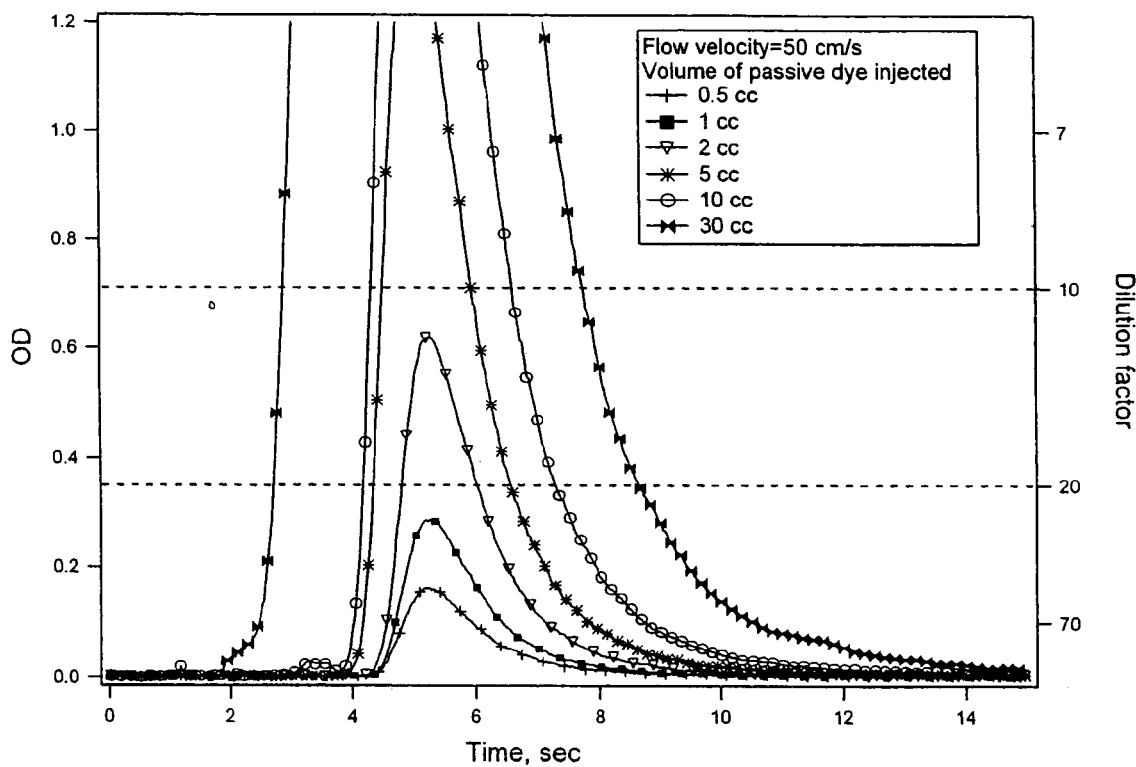
FIG. 20A is a graph of optical density and dilution against time, presenting experimentally derived reagent/sample fluid mixing curves.

The curves in FIG. 20A are based on time-series optical density laboratory measurements, made in a simulated fluids analyzer and flow-line, on reagent and sample fluid mixing for various volumes of reagent injected into sample fluid in a stopped-flow mode. The sample flow-line velocity in the graphs of FIG. 20A is 50 cm/sec.

The graph of FIG. 20A provides an optical density (OD) (left-side scale) and a corresponding dilution factor (right-side scale), of the reagent in the sample, for each volume of reagent in a single injection as a function of time.

In the present invention, a curve is selected whose peak lies between a smaller dilution factor value and a larger dilution factor value, outside of which the dilution factor is too small or too large for the specific analysis being attempted, or the signal to noise ratio is unacceptable.

The selection of an initial volume for execution of step 315 is not critical because adjusting the volume in accordance with steps 318 and 511-513 will produce a suitable value for volume to be inserted. For example, for a pH measurement of a moderately buffered sample using 0.04% phenol red reagent, and a sample flow-line velocity of 50 cm/sec, the 2 cc curve is selected from FIG. 20A because its peak lies between dilution factor=10 and dilution factor=20, the dashed lines in FIG. 20A.

Selection of the volume 2 cc ensures a relatively large number of valid pH measurements (acceptable dilution and good signal to noise ratio), in this case 6 measurements at the rate of 3 measurements per second. The corresponding dilution factor at the peak (11.5 read from the right-side scale) provides the basis for calculating the volume of reagent to be injected.

For a fluids analyzer in accordance with the preferred embodiment of the apparatus, the graph of FIG. 20A may be used to produce a suggested initial value of volume of reagent to be injected (step 414). The graph of FIG. 20A is entered using the standard dilution factor or the standard dilution factor range for the reagent as recommended for use in a laboratory version of the desired measurement. The curve whose peak dilution factor value is smaller than the standard dilution factor, or is within the standard dilution factor range, is selected. A first preliminary value for suitable volume is set equal to the volume associated with the selected peak. To the extent the sample flow-line flow rate is less than or greater than 50 cm/sec, the first preliminary value is increased or reduced to produce a suggested initial value.

It would be possible to select the "5 cc" or higher volume curves and use measurements from two time windows (one before the peak and one after the peak) with acceptable dilution and signal to noise ratio but this would involve consuming more reagent.

The last step in FIG. 4, (417), includes re-starting flow-line pump 51, thereby moving the mixture through the cell of the spectral analyzer, as indicated in FIG. 3 (316).

Optical density of the mixture in the cell of the spectral analyzer is measured to produce a time series of optical density values at multiple wavelengths. See FIG. 3 (317). The measured optical density at each wavelength will change with time in a manner similar to the "2 cc" curve of FIG. 20A.

Because of uncertainties in the actual sample flow-line velocity and the actual reagent-sample mixing patterns in the downhole tool, it is recommended to adjust the volume of reagent to get a suitable dilution and an acceptable signal to noise ratio. See FIG. 3 (318). The process of adjusting the volume to be injected is detailed in steps 512-515 of FIG. 5. The peak OD values at one or more wavelengths are checked to verify that the dilution factor and the signal to noise ratio are acceptable. If the dilution factor and the signal to noise ratio are acceptable, a time series of optical density values at multiple wavelengths measured during this time period is considered valid.

The acceptable range will be different for different reagents and analytical procedures. As noted above, one or more auxiliary reagent containers may be included to provide the ability to select and inject an alternative reagent without requiring withdrawal of the formation tester from the wellbore.

Validated optical density values are stored as time series tables of spectral values. Then these tables of spectral values are used to produce an analysis of formation fluid using conventional spectral analysis techniques. See FIG. 3 (319-320).

The volume of reagent to be injected is determined by syringe pump rate and time. Preferably, the syringe pump rate is fixed, and adjusting the volume of reagent to be injected, involves adjusting an injection time. Alternatively, adjusting the volume of reagent to be injected includes adjusting the syringe pump rate.

Second Embodiment

Reagent-Injected-by-Syringe-Pump, Sample-Flowing Mode

Figure 5:
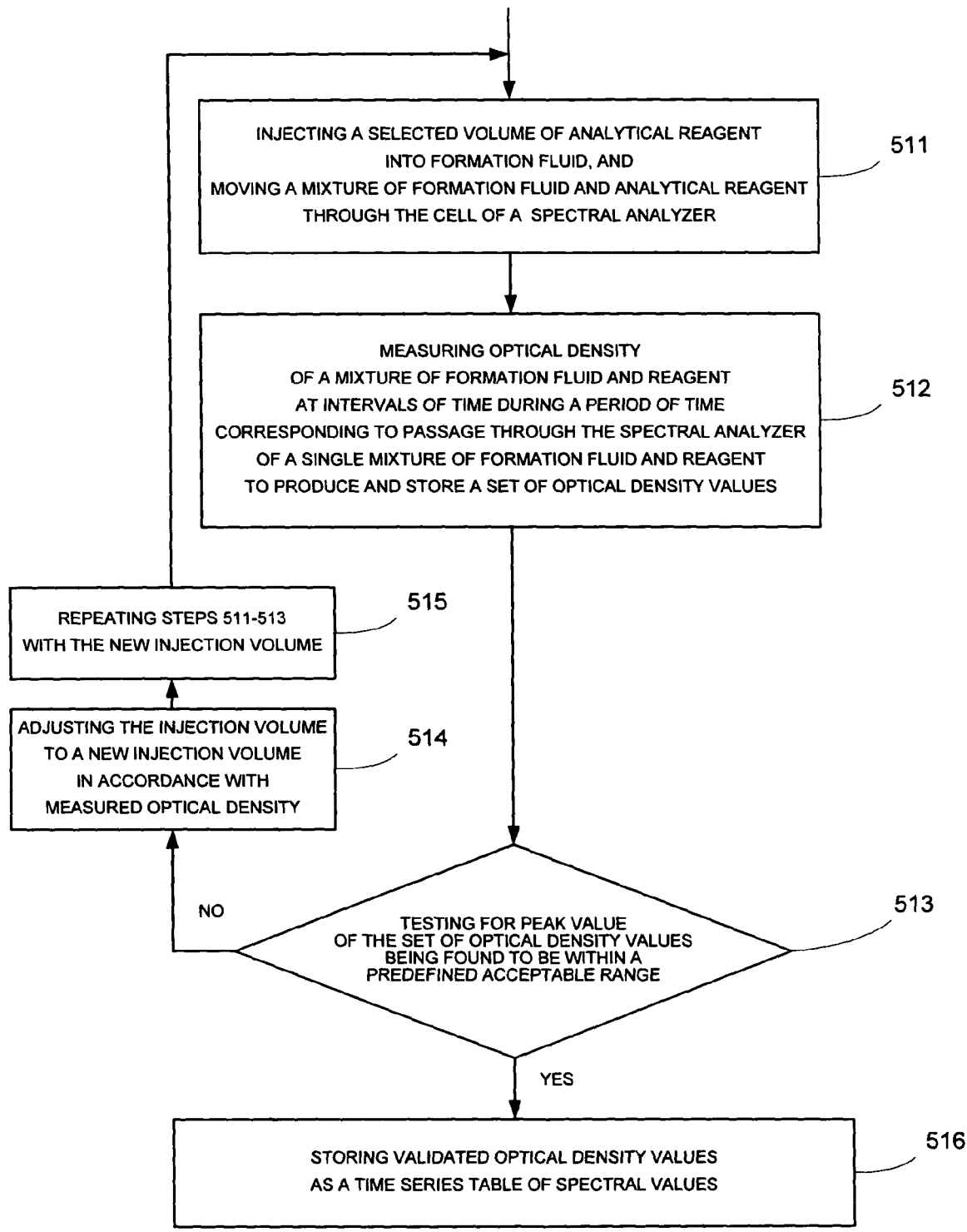
Figure 6:
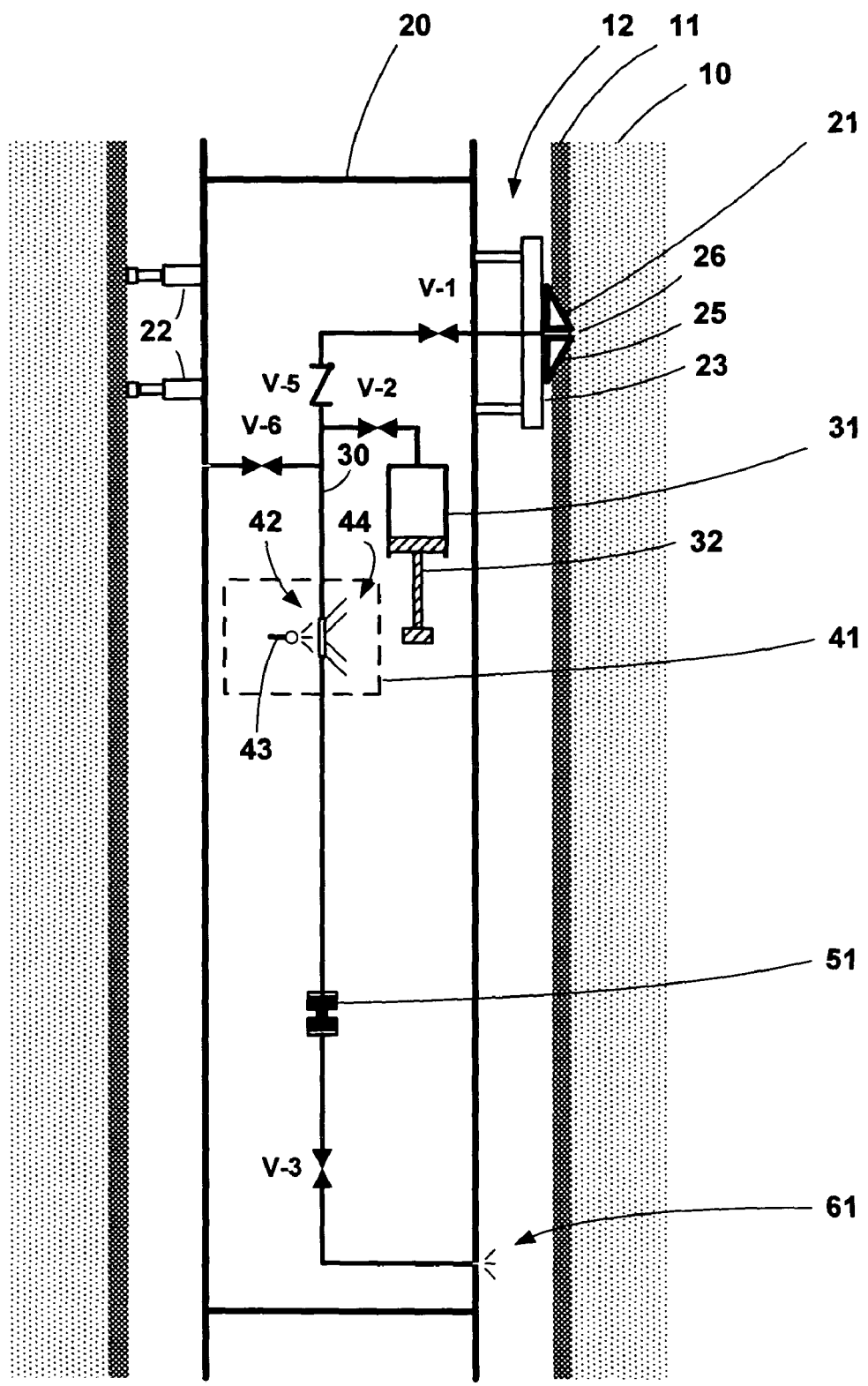
FIG. 6 shows detail of a second embodiment of the fluids analyzer, including the apparatus of FIG. 2, plus a check valve, and a safety relief valve, the fluids analyzer configured for executing the steps of a second embodiment of the method.
Figure 7:
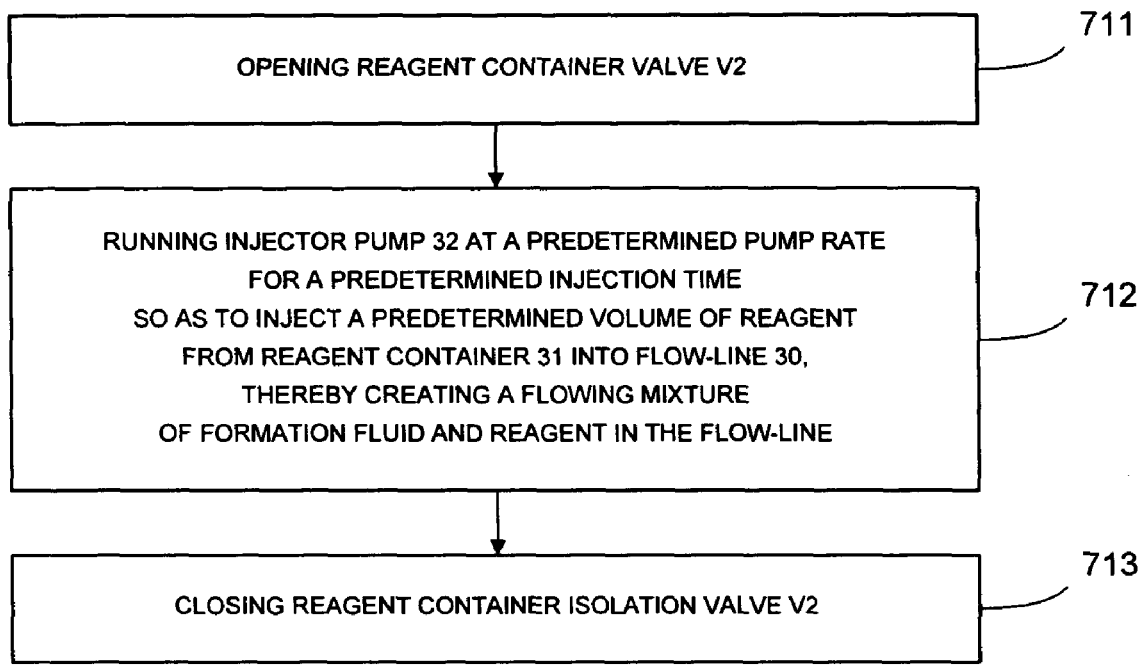
FIG. 7 is a flowchart illustrating the second embodiment of the method of the invention, the method including reagent injection spectral analysis operating in a reagent-injected-by-syringe-pump, continuous-flow mode.

The second embodiment of the invention is illustrated in FIG. 6 (apparatus) and FIGS. 7, 3 and 5 (method).

FIG. 6 shows fluids analyzer 20 configured for operation of the second embodiment. The configuration of FIG. 6 includes all except valve V4 of the elements of FIG. 2 including injector pump 32, plus check valve V5 and a pressure-release safety valve V6. Check valve V5 prevents back flow of reagent through the open isolation valve V1. V6 is a pressure-release safety valve needed to relieve excess pressure across check valve V5 when the formation tester is brought to the surface.

FIG. 7 shows the method of the second embodiment using reagent injection spectral analysis operating in reagent-injected-by-syringe-pump, sample-flowing mode. The method of the second embodiment applies steps 315 and 316 of FIG. 3 as executed by the steps of FIG. 7. Referring to FIG. 6, the method includes running injector pump 32 at a second selected pump rate for a predetermined injection time so as to inject a defined volume of reagent from reagent container 31 into flow-line 30. This creates a flowing mixture of formation fluid and reagent in the flow-line. Adjusting the volume of reagent to be injected, as required by step 318 of FIG. 3, and as executed by the steps of FIGS. 5 and 7, involves adjusting an injection time or adjusting the pump rate of the syringe pump.

Third Embodiment

Reagent-Injected-by-Wellbore-Pressure, Uncontrolled, Sample-Stopped Mode

Figure 8:
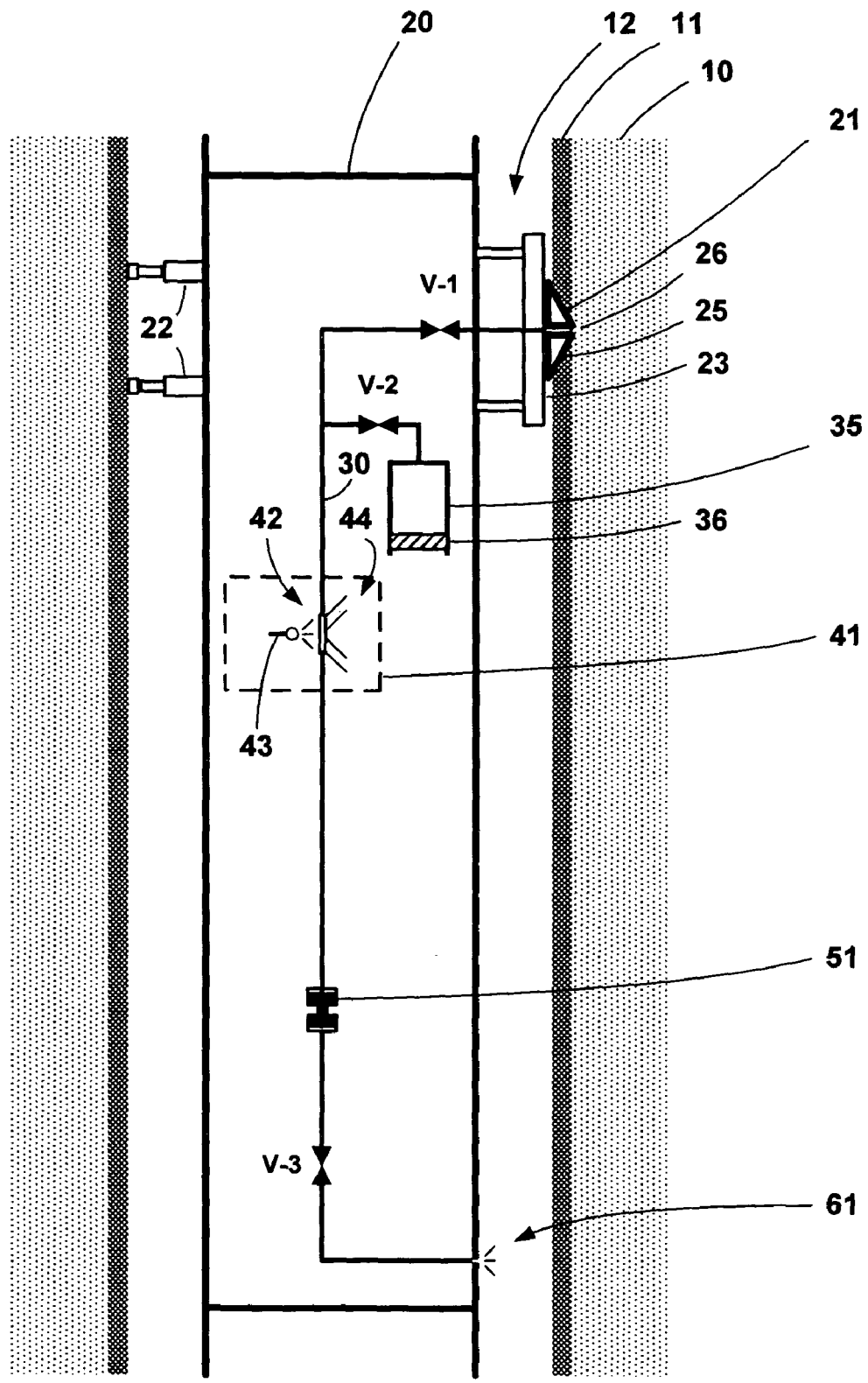
FIG. 8 shows detail of a third embodiment of the fluids analyzer, the fluids analyzer including a passive reagent container, the fluids analyzer configured for executing the steps of a third embodiment of the method.
Figure 9:
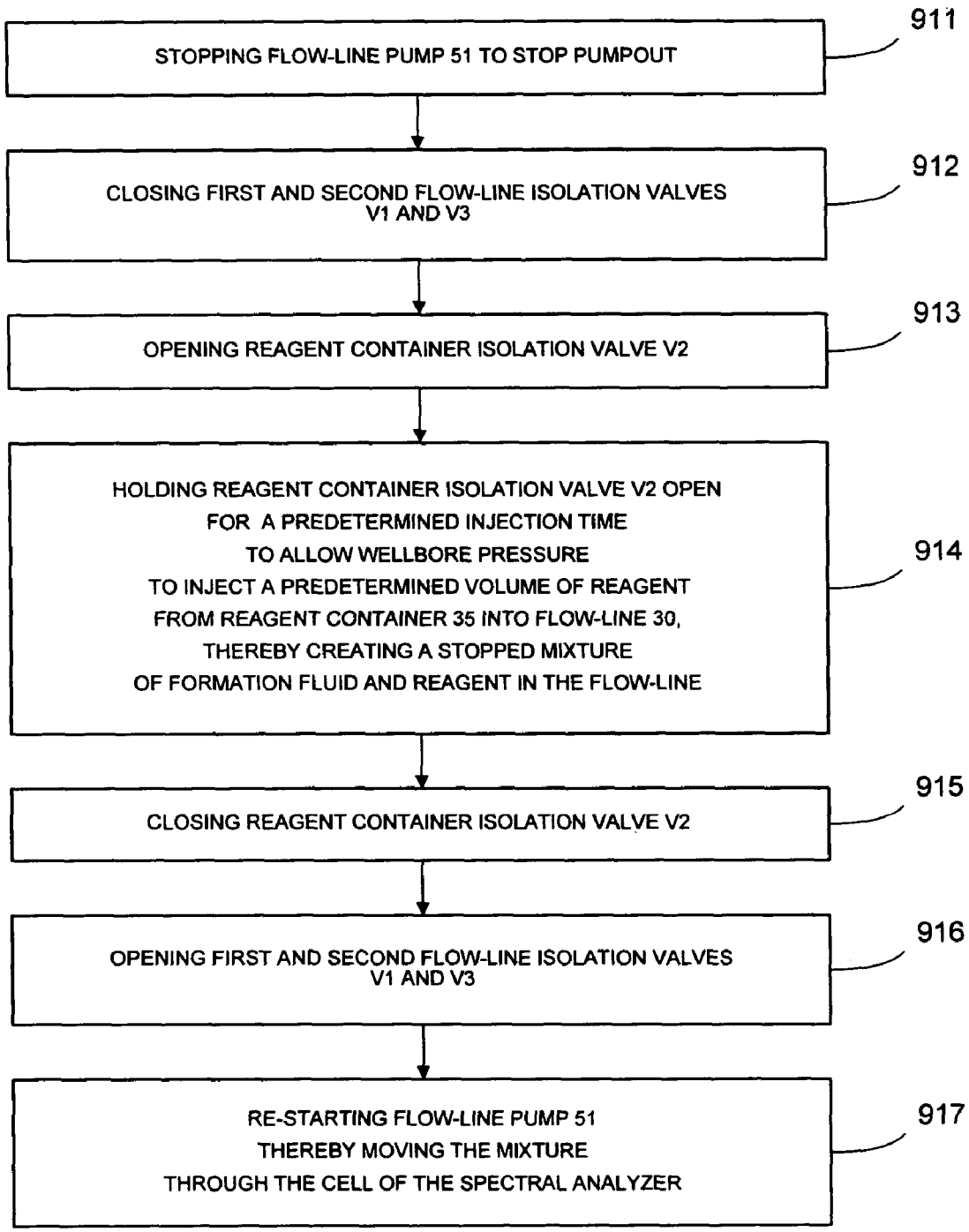
FIG. 9 is a flowchart illustrating the third embodiment of the method of the invention, the method including reagent injection spectral analysis operating in a reagent-injected-by-wellbore-pressure, uncontrolled, sample-stopped mode.

The third embodiment of the invention is illustrated in FIG. 8 (apparatus) and FIGS. 9 and 3 (method).

FIG. 8 shows fluids analyzer 20 configured for operation in reagent-injected-by-wellbore-pressure, uncontrolled, sample-stopped mode. FIG. 8 shows a passive reagent container 35, i.e. a reagent container without the syringe pump of FIG. 2. FIG. 8 also shows a pressure-coupler (passive piston) 36, and reagent container isolation valve V2. Passive piston 36 is continually exposed to wellbore pressure. Container 35 has a reagent capacity of approximately 4 liters, of which a reagent volume of approximately 2-5 cc will transfer into the stopped volume of the flow-line, the reagent volume set by the difference between wellbore pressure and flow-line pressure, the stopped volume, and fluid compressibility. The stopped volume is the volume enclosed between isolation valve V1 and pump 51.

The method of the third embodiment applies steps 315 and 316 of FIG. 3 as executed by the steps of FIG. 9. The method uses reagent injection spectral analysis operating in a reagent-injected-by-wellbore-pressure, uncontrolled, sample-stopped mode, using the difference between wellbore pressure and flow-line pressure to insert reagent. The method of the third embodiment includes holding reagent container isolation valve V2 open for a predetermined injection time to allow the difference between wellbore pressure and flow-line pressure to inject reagent from reagent container 35 into flow-line 30. This creates a stopped mixture of formation fluid and reagent in the flow-line. When using wellbore pressure injection in stopped-flow mode, the ability to adjust the volume of analytical reagent is limited, so step 318 of FIG. 3 is omitted and step 319 is limited to "storing optical density values as a time series table of spectral values" because the optical density values are not validated.

Fourth Embodiment

Reagent-Injected-by-Wellbore-Pressure, Restrictor-Limited, Sample-Flowing Mode

Figure 10:
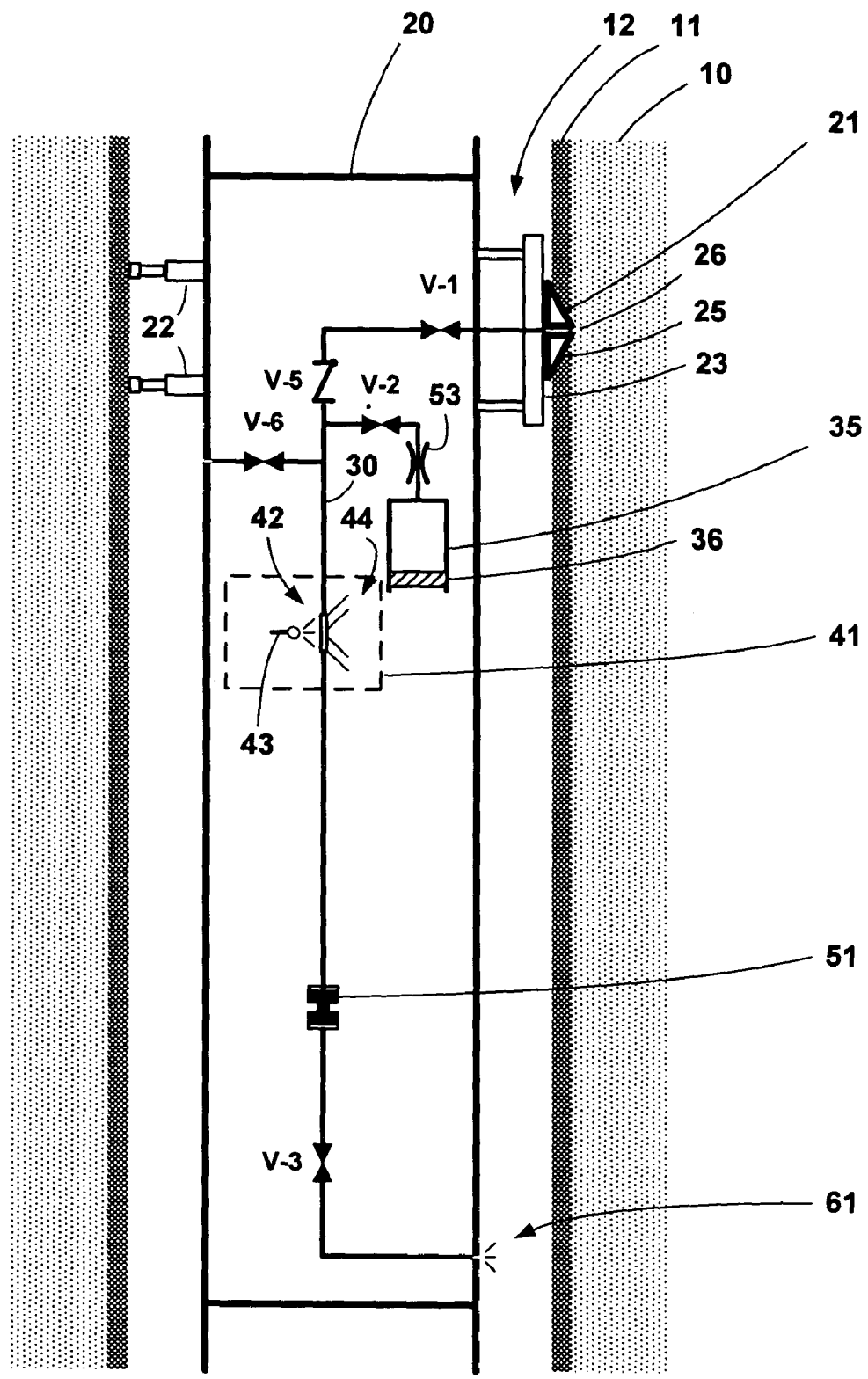
FIG. 10 shows detail of a fourth embodiment of the fluids analyzer configured for executing the steps of a fourth embodiment of the method by including a passive reagent container with a restrictor at its outlet.
Figure 11:
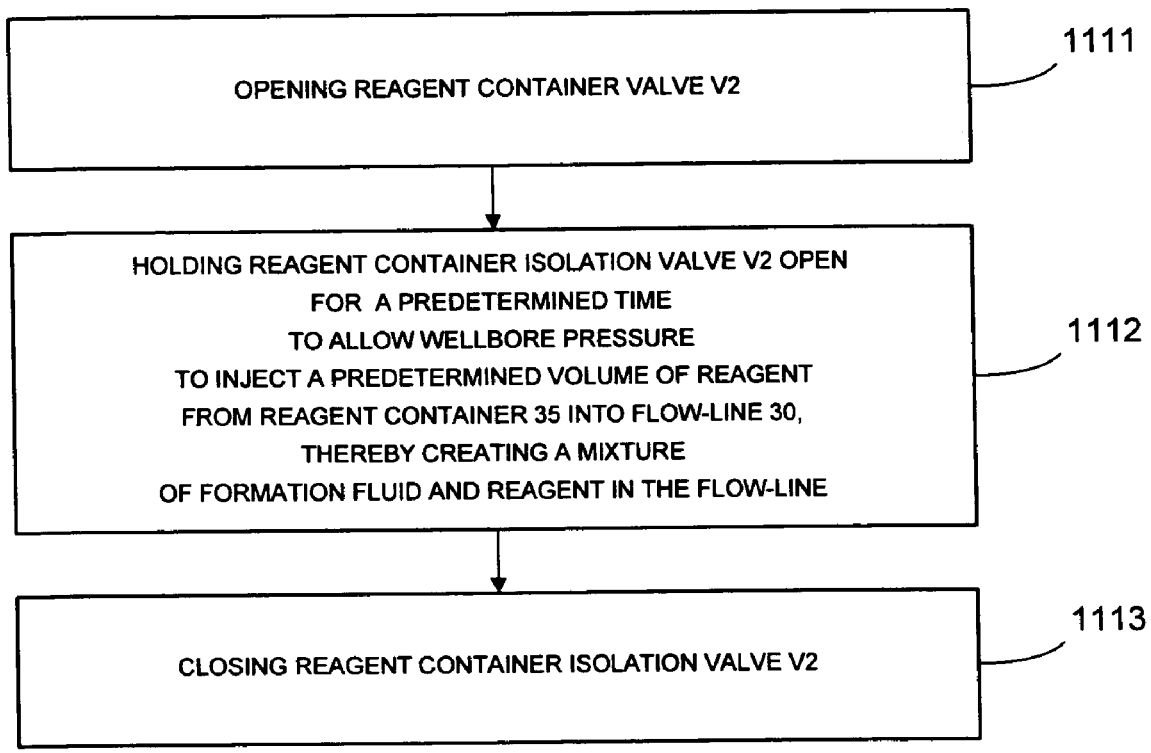
FIG. 11 is a flowchart illustrating the fourth embodiment of the method of the invention, the method including reagent injection spectral analysis operating in reagent-injected-by-wellbore-pressure, restrictor-limited, sample-flowing mode.

The fourth embodiment of the method of the invention is illustrated in FIG. 10 (apparatus) and FIGS. 11, 3 and 5 (method).

FIG. 10 shows fluids analyzer 20 configured for operation of the fourth embodiment of the method. FIG. 10 shows a reagent container 35 with a pressure-coupler (passive piston) 36, an isolation valve V2, and a restrictor 53. FIG. 10 also shows check valve V5 and a pressure-release safety valve V6. As in the second embodiment, check valve V5 prevents back flow of reagent through the open isolation valve V1, and V6 is a pressure-release safety valve needed to relieve excess pressure across check valve V5 when the formation tester is brought to the surface.

FIG. 10 illustrates a fourth embodiment of the method of the invention. The method of the fourth embodiment applies steps 315 and 316 of FIG. 3 as executed by the step 112 of FIG. 11. The method uses reagent injection spectral analysis operating in reagent-injected-by-wellbore-pressure, restrictor-limited, sample-flowing mode. Injection is by wellbore pressure via restrictor 53 and isolation valve V2. The method of the fourth embodiment includes holding isolation valve V2 open for a predetermined injection time to allow wellbore pressure to inject a controlled volume of reagent from reagent container 35 into stopped formation fluid in flow-line 30. This creates a mixture of formation fluid and reagent in the flow-line. Adjusting the volume of reagent, as indicated in step 318 of FIG. 3 and steps 512-515 of FIG. 5, includes executing the steps of FIG. 11. In the fourth embodiment this includes adjusting the injection time.

Fifth Embodiment

Reagent-Injected-by-Wellbore-Pressure, Throttle-Controlled, Sample-Flowing Mode

Figure 12:
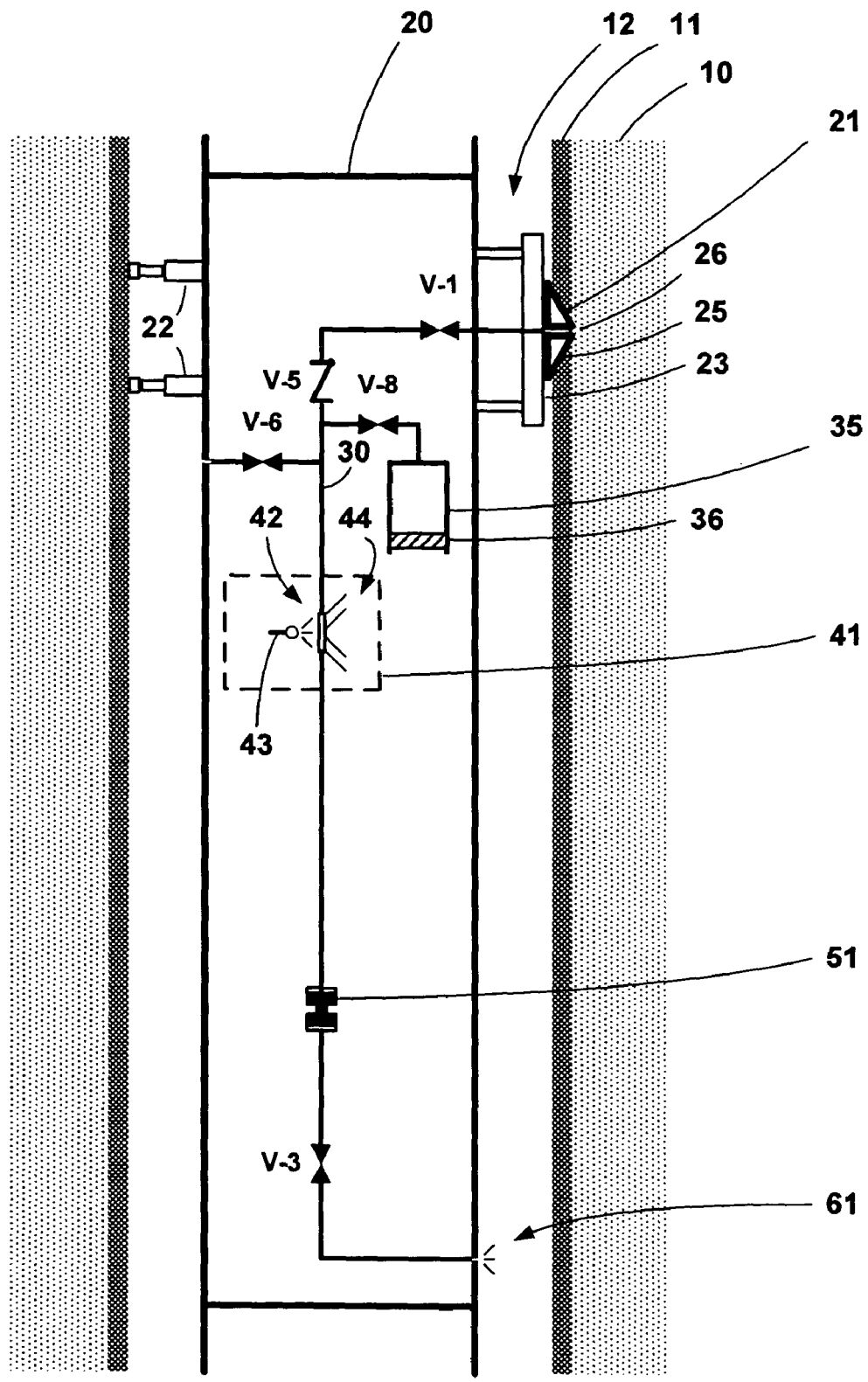
FIG. 12 shows detail of a fifth embodiment of the fluids analyzer, the fluids analyzer including a reagent container with a pressure-coupler (passive piston) and a throttle valve, the fluids analyzer configured for executing the steps of a fifth embodiment of the method.
Figure 13:
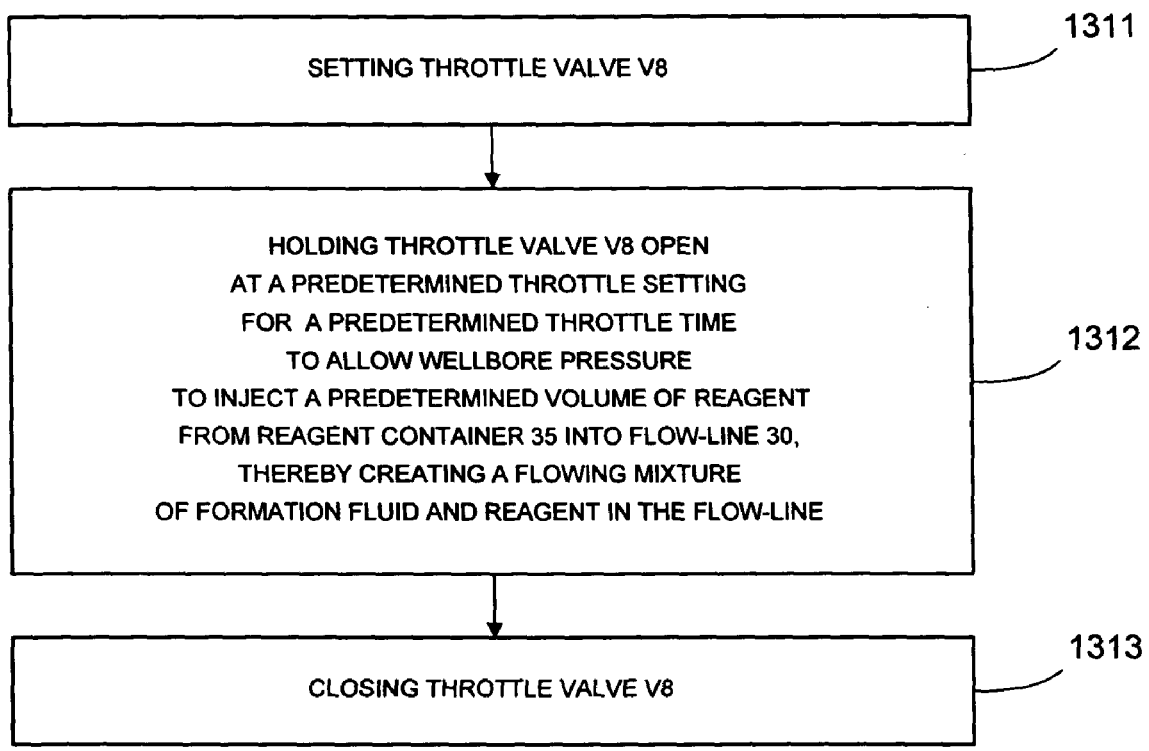
FIG. 13 is a flowchart illustrating the fifth embodiment of the method of the invention, the method including reagent injection spectral analysis operating in reagent-injected-by-wellbore-pressure, throttle-controlled, sample-flowing mode.

The fifth embodiment of the method of the invention is illustrated in FIG. 12 (apparatus) and FIGS. 13, 3 and 5 (method).

FIG. 12 shows fluids analyzer 20 configured for operation of the fifth embodiment of the method. FIG. 12 shows a reagent container 35 with a pressure-coupler (passive piston) 36, as in FIGS. 8 and 10, and with a throttle valve V8. FIG. 12 also shows check valve V5 and a pressure-release safety valve V6. As in the second embodiment, check valve V5 prevents back flow of reagent through the open isolation valve V1. V6 is a pressure-release safety valve needed to relieve excess pressure across check valve V5 when the formation tester is brought to the surface.

FIG. 13 illustrates a fifth embodiment of the method of the invention. The method of the fifth embodiment applies steps 315 and 316 of FIG. 3 as executed by the step 1312 of FIG. 13. The method uses reagent injection spectral analysis operating in reagent-injected-by-wellbore-pressure, throttle-controlled, sample-flowing mode. Injection is by wellbore pressure via throttle valve V8. The method of the fourth embodiment includes holding throttle valve V8 open at a predetermined throttle-valve setting for a predetermined throttle-valve injection time to allow wellbore pressure to inject a controlled volume of reagent from reagent container 35 into formation fluid flowing in flow-line 30. This creates a flowing mixture of formation fluid and reagent in the flow-line. Adjusting the volume of reagent in step 318 of FIG. 3 and steps 512-515 of FIG. 5 includes executing the steps of FIG. 13. In the fifth embodiment this includes adjusting the volume to a new injection volume by adjusting one or both of the throttle setting of throttle valve V8 and the injection time.

Sixth Embodiment

Reagent-Injected-by-Sample-Extraction, Syringe-Pump, Sample-Stopped Mode

Figure 14:
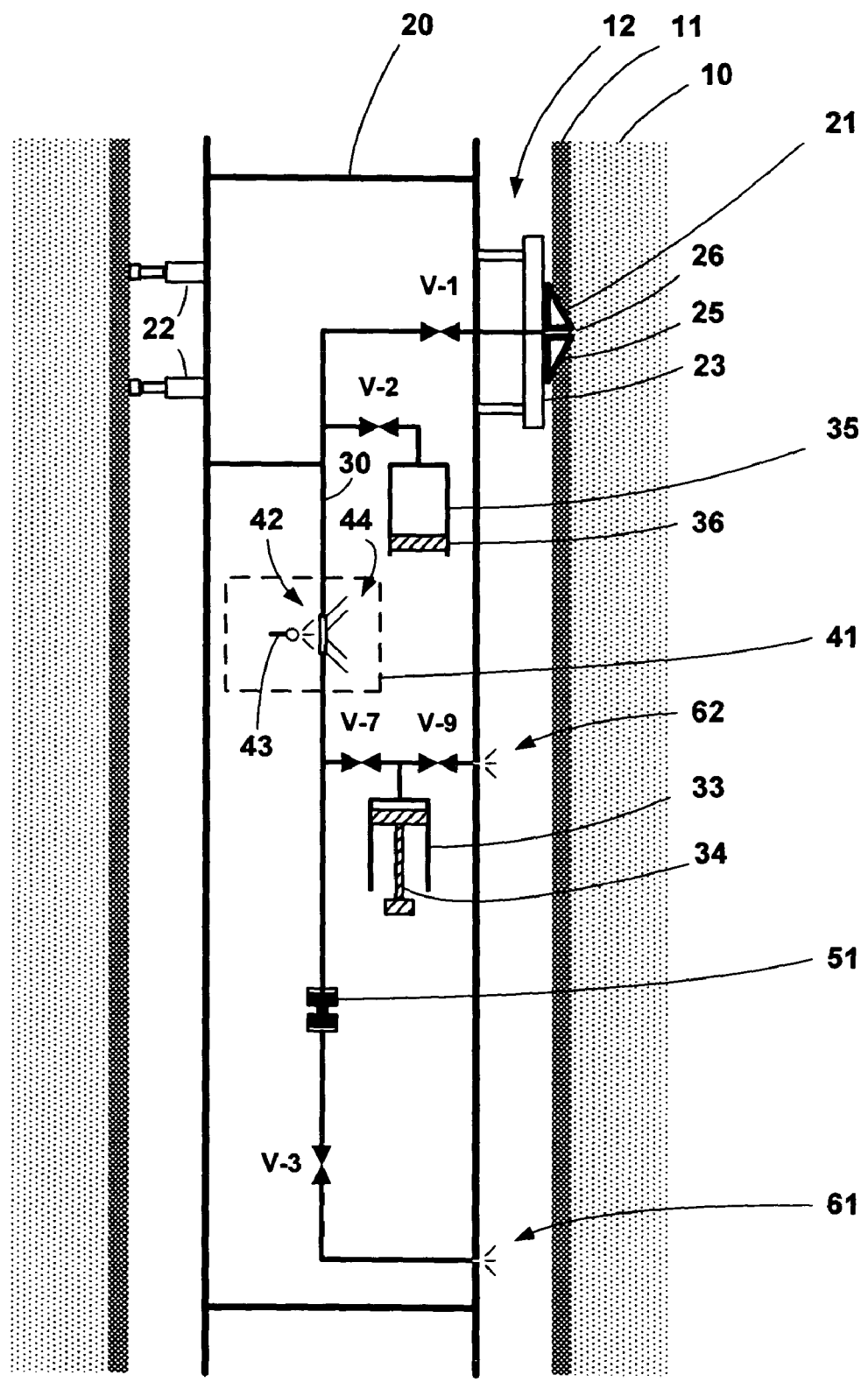
FIG. 14 shows detail of a sixth embodiment of the fluids analyzer, including a reagent container with a pressure-coupler (passive piston) and a fluid container 33 with an extractor pump (syringe pump), the fluids analyzer configured for executing the steps of a sixth embodiment of the method.
Figure 15:
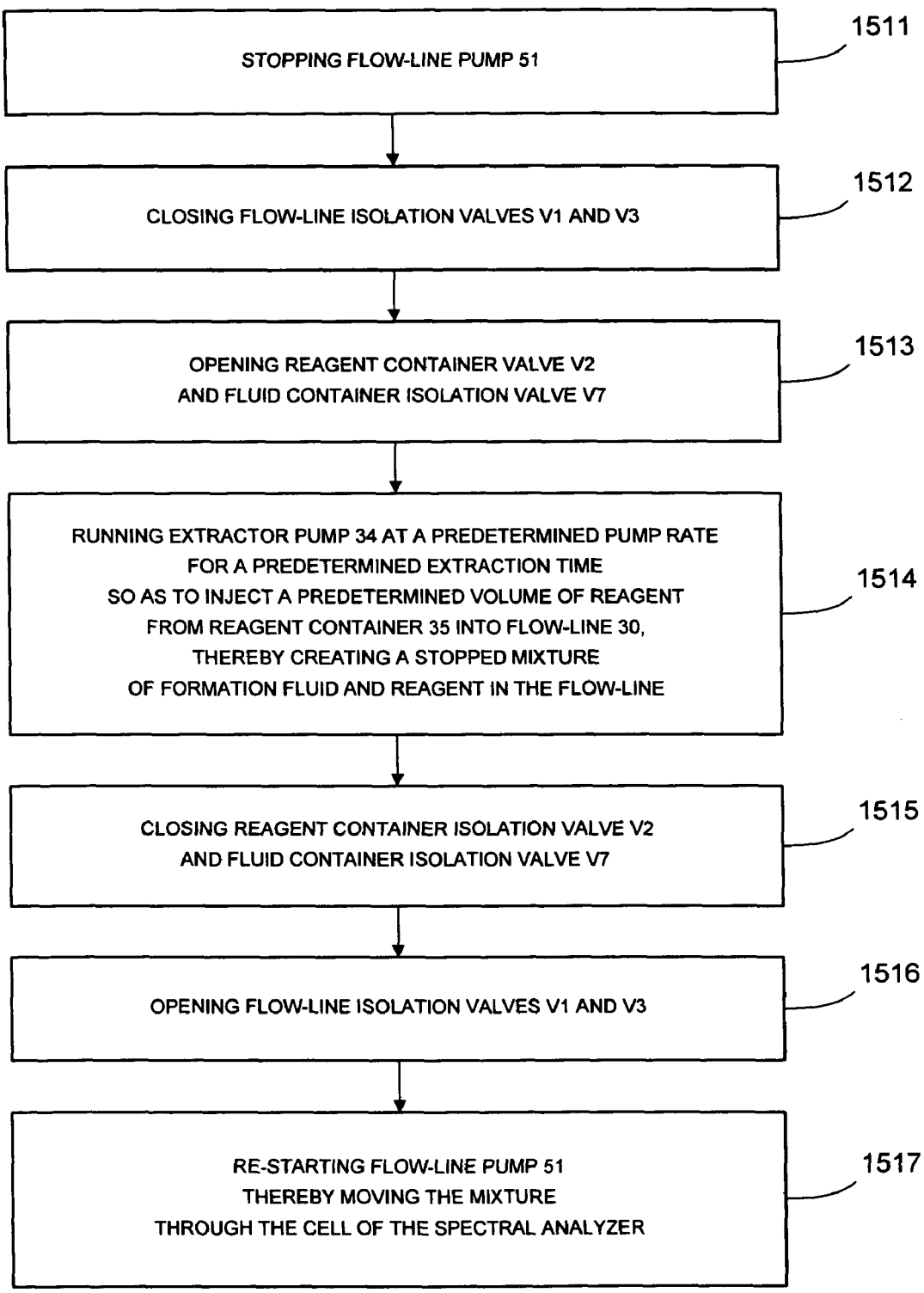
FIG. 15 is a flowchart illustrating the sixth embodiment of the method of the invention, the method including reagent injection spectral analysis operated in a reagent-injected-by-sample-extraction, syringe-pump, sample-stopped mode.

The sixth embodiment of the method of the invention is illustrated in FIG. 14 (apparatus) and FIGS. 15, 3 and 5 (method).

FIG. 14 shows fluids analyzer 20 configured for operation of the sixth embodiment of the method. The configuration of FIG. 14 includes reagent container 35 with pressure-coupler (passive piston) 36, fluid container 33 with an extractor pump (syringe pump) 34, isolation valve V7, and discharge valve V9. Fluid is drawn into fluid container 33 via isolation valve V7 and is discarded downhole via discharge valve V9 and auxiliary pump-out line 62.

FIG. 15 illustrates a sixth embodiment of the method of the invention. The sixth embodiment uses reagent injection spectral analysis operating in reagent-injected-by-sample-extraction, syringe-pump, sample-stopped mode. Referring to FIG. 14, the method of the sixth embodiment includes running extractor pump 34 at a selected pump rate for a selected extraction time so as to inject a defined volume of reagent from reagent container 35 into formation fluid in flow-line 30. This creates a stopped mixture of formation fluid and reagent in the flow-line. As in the first embodiment, the volume of reagent to be injected is determined by syringe pump rate and time. Preferably, the syringe pump rate is fixed, and adjusting the volume of reagent to be injected involves adjusting an injection time. Alternatively, adjusting the volume of reagent to be injected includes adjusting the syringe pump rate.

Seventh Embodiment

Reagent-Injected-by-Sample-Extraction, Main-Pump, Sample-Stopped Mode

Figure 16:
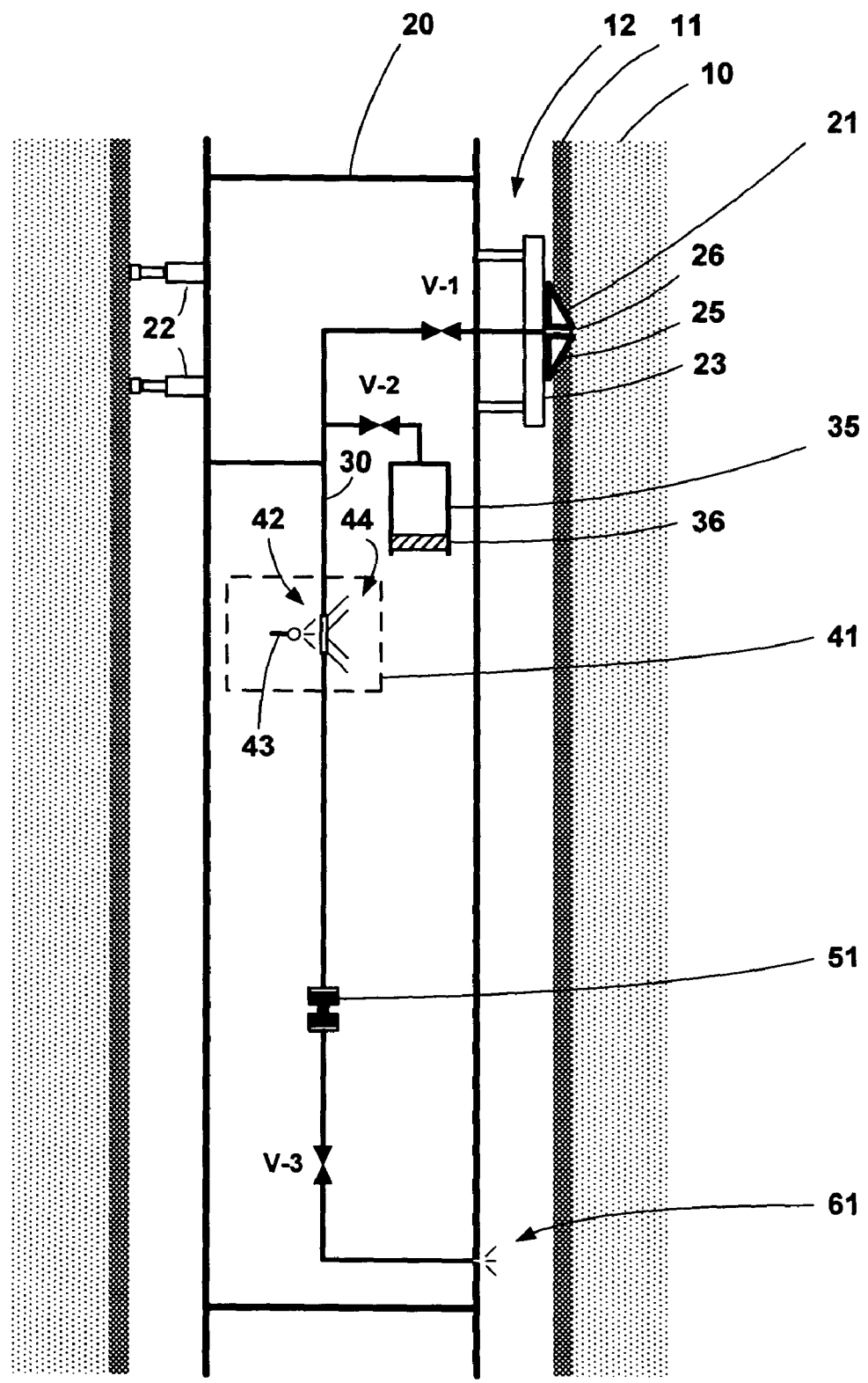
FIG. 16 shows detail of a seventh embodiment of the fluids analyzer, including a reagent container with a pressure-coupler (passive piston), the fluids analyzer configured for executing the steps of a seventh embodiment of the method.
Figure 17:
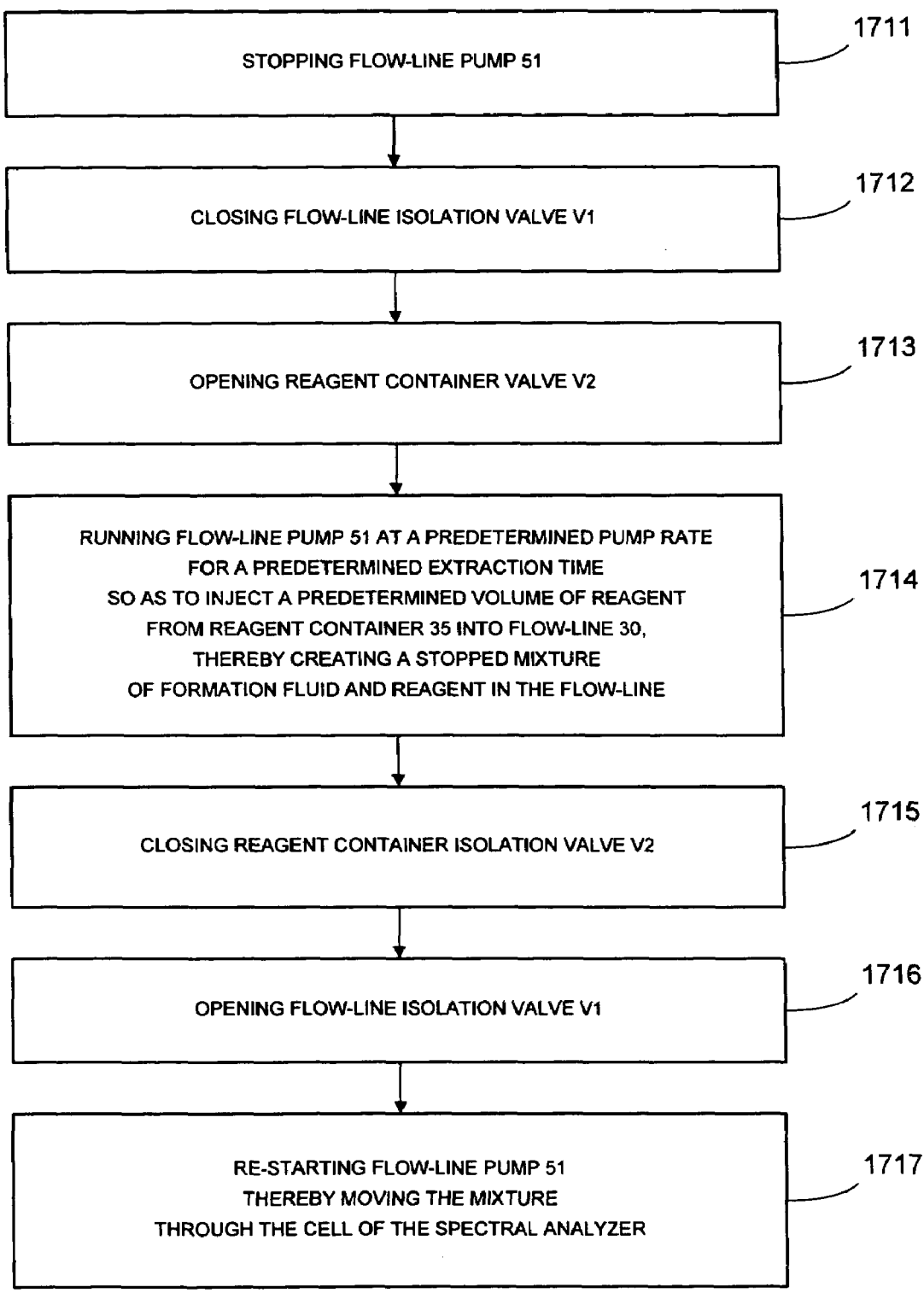
FIG. 17 is a flowchart illustrating the seventh embodiment of the method of the invention, the method including reagent injection spectral analysis operated in a reagent-injected-by-sample-extraction, main-pump, sample-stopped mode.

The seventh embodiment of the method of the invention is illustrated in FIG. 16 (apparatus) and FIGS. 17, 3 and 5 (method).

FIG. 16 shows fluids analyzer 20 configured for operation of the seventh embodiment of the method. The configuration of FIG. 16 includes passive reagent container 35 with pressure-coupler (passive piston) 36, and uses flow-line pump 51 to draw reagent from the reagent container into the flow-line, thereby indirectly injecting reagent.

FIG. 17 illustrates a seventh embodiment of the method of the invention. The seventh embodiment uses reagent injection spectral analysis operating in reagent-injected-by-sample-extraction, main-pump, sample-stopped mode. Referring to FIG. 16, the method of the fifth embodiment includes running flow-line pump 51 at a selected pump rate for a selected extraction time so as to inject a defined volume of reagent from reagent container 35 into formation fluid in flow-line 30. This creates a stopped mixture of formation fluid and reagent in the flow-line. The volume of reagent to be injected is determined by the pump rate and time of pump 51 during step 1714 of FIG. 17. After opening isolation valve V1 and restarting pump 51 (steps 1716-1717), and after the mixture has passed through the spectral analyzer, the mixture is discarded downhole via isolation valve V3 and main pump-out line 61.

Eighth Embodiment

Reagent-Injected-by-Sample-Extraction, Step-Piston, Sample-Stopped Mode

Figure 18:
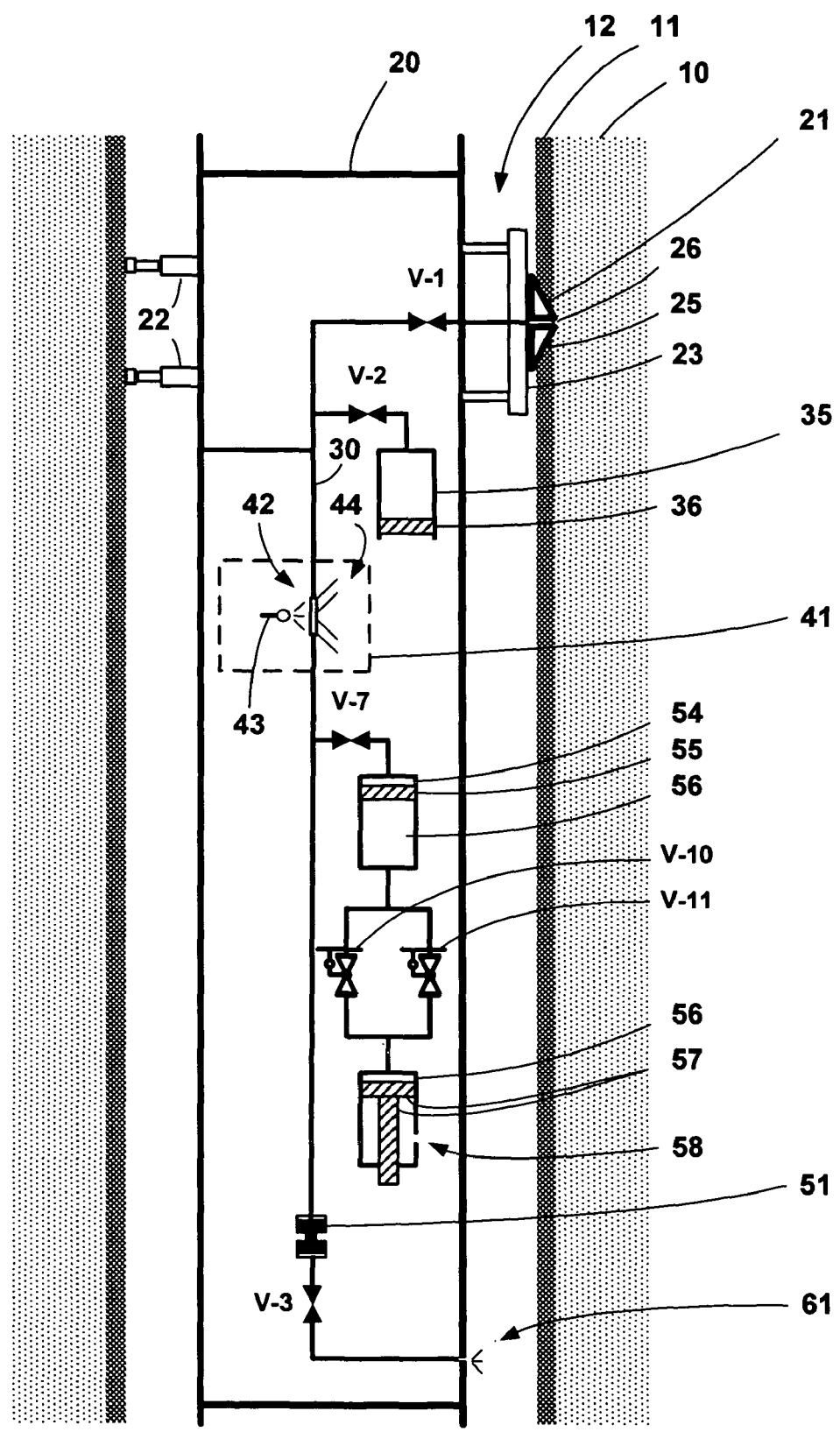
FIG. 18 shows detail of a eighth embodiment of the fluids analyzer, including a passive reagent container including a pressure-coupler (passive piston), a fluid container, and a step piston, the fluids analyzer configured for executing the steps of a eighth embodiment of the method.
Figure 19:
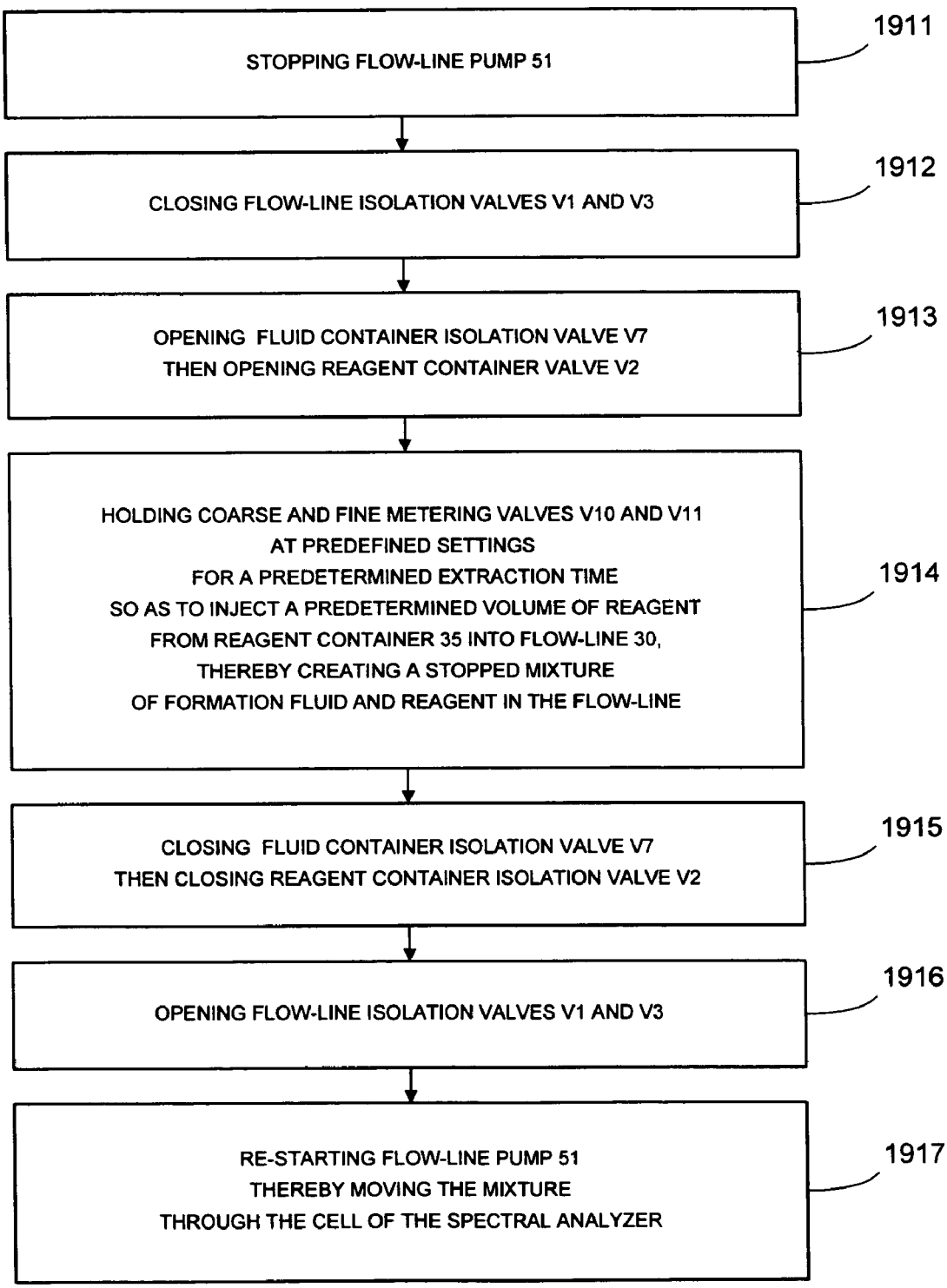
FIG. 19 is a flowchart illustrating the eighth embodiment of the method of the invention, the method including reagent injection spectral analysis operated in a reagent-injected-by-sample-extraction, step-piston, sample-stopped mode.

The eighth embodiment of the method of the invention is illustrated in FIG. 18 (apparatus) and FIGS. 19, 3 and 5 (method).

FIG. 18 shows fluids analyzer 20 configured for operation of the eighth embodiment of the method. The configuration of FIG. 18 includes passive reagent container 35 including pressure-coupler (passive piston) 36 and fluid container 54 including pressure-coupler (passive piston) 55, and a step piston 57. Step piston 57 is coupled to fluid container 54 via hydraulic fluid 56 passing through adjustable coarse and fine metering valves V10 and V11. Step piston 57 is also coupled to wellbore pressure via pressure coupling 58. Step piston 57 is driven to draw fluid into fluid container 54. It is driven by substantially equal pressures applied to substantially unequal areas on opposite sides of the piston. Step piston 57 operates to draw sample into fluid container 54 from the flow-line via isolation valve V7, thereby causing injection of reagent from reagent container 35 into the flow-line. This creates a stopped mixture of formation fluid and reagent in the flow-line. The structure and operation of an apparatus (prior art) similar to step piston 57 is disclosed in U.S. Pat. No. 6,058,773 (item 15, FIG. 7).

FIG. 19 illustrates an eighth embodiment of the method of the invention. The eighth embodiment uses reagent injection spectral analysis operating in reagent-injected-by-sample-extraction, step-piston, sample-stopped mode. Referring to FIG. 18, the method of the eighth embodiment includes running step piston 57 to inject a predetermined volume of reagent. The volume of reagent to be injected is determined by piston speed and time. Piston speed is controlled by setting coarse and fine metering valves V10 and V11. Piston speed and time are set so as to inject a predetermined volume of reagent from reagent container 35 into formation fluid in flow-line 30. This creates a stopped mixture of formation fluid and reagent in the flow-line.

Experimental Results

FIG. 20A is a graph of optical density and dilution against time, presenting experimentally derived reagent/sample fluid mixing curves for a flow-line velocity of 50 cm/sec. It shows kinetic scans of a pH-insensitive tracer dye absorbance (OD) and dilution of reagent in the sample as a function of dye injection volume. The laboratory set-up simulated a downhole configuration similar to the first embodiment of the present invention. The injection point was 232 cm upstream of the optical detector. The flow-line internal diameter was 0.635 cm. The optical cell path length was 0.26 cm. A fixed volume of dye was injected into the flow-line with the flow stopped. Kinetic scan and fluid flow were started simultaneously immediately following the injection of reagent at t=0. The absorbance at 629 nm was recorded as a function of time by the downstream optical detector. The detection system used had a saturation limit of about 1.2 units, beyond which the signal to noise ratio was very poor. The kinetic scan was done at the maximum data acquisition speed of 0.033 seconds. The measured optical densities can be scaled to dye dilution factors as shown on the right axis. Dilution factor is defined as ratio of concentration of reagent in reagent container to concentration of reagent in mixed stream. For a given tool configuration, the dilution factors can be changed by changing reagent injection volume, flow-line sample velocity, or reagent concentration in container. Mixing curves can be used to select volume of reagent to be injected to get appropriate dilution factors.

The pH of an unknown solution may be obtained spectroscopically using the equation below (R. G. Bates, Determination of pH: Theory and Practice, Chapter 6, John Wiley, 1964):

$$\text{pH} = pK_a + \log\frac{\gamma_B}{\gamma_A} + \log\frac{B}{A} \qquad \text{Eq. 1}$$

where $K_a$ is the thermodynamic equilibrium constant for the pH sensitive dye (reagent) added to the sample and is a function of temperature; A and B are the respective fractions of the acid and base forms of the pH sensitive dye; and $\gamma_A$ and $\gamma_B$ are respective activity coefficients of the acid and base forms of the dye, and depend on ionic strength of the solution and temperature. Both $K_a$ and activity coefficients could be weak functions of pressure as well.

The fraction of the dye that exists in the acid form (A) and base form (B) are measured spectroscopically. The pH calculation depends only on the ratio of B to A and is independent of the absolute concentration of the dye. The only constraint on the dye concentration in sample is that, depending on the buffering strength of the aqueous sample, there is an upper limit to the concentration of the dye beyond which the addition of the dye will affect the pH of the sample being measured. The lower limit on the dye concentration is set by the accuracy of the spectrophotometer and signal to noise ratio of the measurement. If the acid and base optical densities are very low, the poor signal to noise ratio will result in large errors in calculated pH. For typical formation waters and the optical detectors deployed in downhole formation tools, acceptable dye concentrations in fluid samples would typically fall in the range of $10^{-5}$M to $10^{-4}$M. The range of acceptable dilution factors, and hence the volume of dye to be injected, can be estimated as a function of the dye concentration in the reagent container and expected sample flow-line velocity using mixing curves such as shown in FIG. 20A. For example, using a 0.04% phenol red reagent, a peak dilution factor of 10-20 would be acceptable for a 0.2 cm path length and moderate buffer strength of the sample. These limits are shown as the dashed lines in FIG. 20A for flow-line velocity of 50 cm/sec. Hence for a 0.04% phenol red reagent and sample flow-line velocity of 50 cm/sec for example, results from FIG. 20A would suggest that an initial selected injection volume be at least 2 cc. Data from about 4.8 seconds to 7 seconds can be used for pH calculation. Beyond 7 seconds, the dye concentration may be too low and the signal to noise ratio poor. If the volume is higher, for example 5 cc, then the region with dilution factor less than 10 around the peak (4.5 to 6 seconds) can be neglected when processing the data to calculate pH as here the reagent concentration is more than $10^{-4}$M. However, data from 4 to 4.5 seconds can still be used, as can data from beyond about 6 seconds, where the dilution factor is acceptable again, to about 8 seconds. Beyond 8 seconds the signal to noise ratio deteriorates. Thus beyond 2 cc, the volume of injection is not critical in this example. Even an injection of 30 cc is acceptable, as suitable time-windows could still be selected, but this would consume more reagent. When a pH sensitive dye such as phenol red is injected, the downhole detector would record at least two kinetic optical density scans simultaneously; one for the base form of the dye at 559 nm (Base OD(t)) and another for the acid form of the dye at 432 nm (Acid OD(t)). While Base OD(t) and Acid OD(t) are functions of time, and depend on dye quantity injected and the flow rate, the ratio of Base OD(t) to Acid OD(t) is a constant and depends only on pH of the sample as seen in FIG. 20B.

Figure 20B:
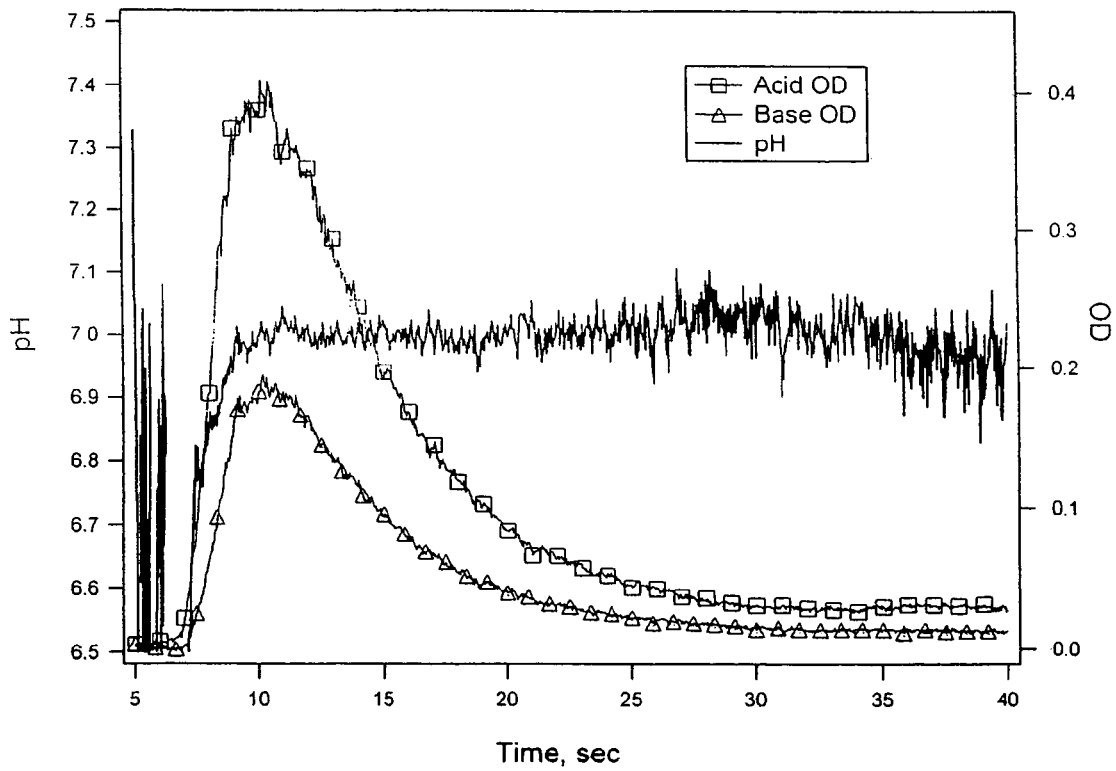
FIG. 20B is a graph of pH and optical density against time.

FIG. 20B shows laboratory measurement of pH of a buffer 7 solution using 0.04% phenol red reagent. The sample flow-line velocity is 16.67 cm/sec and the reagent injection volume is 5 cc. The detector tracks the optical density of the acid and base fractions as the reagent-water mixture flows by it. The peak OD values for the two channels are used to validate the volume of dye injected. The acid and base concentrations can be calculated from the optical density. Then pH can be calculated using Eq. 1 above. Note how the error in calculated pH increases as the signal to noise ratio for the optical densities in these two channels become unacceptable beyond about 25 seconds.

What is claimed is:

1. A method for analyzing formation fluid in an earth formation surrounding a borehole, the method comprising:
   in a formation tester having a reagent container coupled to a fluids analyzer via a flow line, storing analytical reagent in the reagent container;
   transporting the formation tester downhole;
   drawing formation fluid into the flow-line at least once such that the formation fluid is in communication with the fluids analyzer whereby the fluids analyzer establishes a baseline analysis;
   while the formation tester remains downhole, mixing a predetermined amount of the analytical reagent with the formation fluid in view of the formation fluid baseline analysis;
      moving a reacted mixture of formation fluid and analytical reagent fluid through a spectral analyzer cell in the fluids analyzer; and
      performing spectral analysis on the reacted mixture while downhole.

2. The method according to claim 1, wherein the step of mixing the analytical reagent with the formation fluid comprises injecting analytical reagent into formation fluid within the flow-line to create the mixture of formation fluid and analytical reagent in the flow-line.

3. The method according to claim 2, wherein injecting analytical reagent comprises injecting a predetermined volume of analytical reagent.

4. The method according to claim 3, wherein injecting the predetermined volume of the reagent comprises adjusting an injection period of time.

5. The method according to claim 3, wherein injecting the predetermined volume of the reagent comprises adjusting an injection pump rate.

6. The method according to claim 3, wherein injecting analytical reagent comprises injecting analytical reagent into a stopped formation fluid.

7. The method according to claim 3, wherein injecting reagent comprises injecting reagent into a flowing formation fluid.

8. The method according to claim 2, wherein injecting reagent comprises injecting reagent using wellbore overpressure.

9. The method according to claim 8, wherein injecting reagent comprises injecting reagent at a controlled rate using a restrictor.

10. The method according to claim 8, wherein injecting reagent comprises injecting reagent at a controlled rate using a throttle valve.

11. The method according to claim 8, wherein injecting reagent comprises injecting reagent for a controlled period of time.

12. The method according to claim 2, wherein injecting analytical reagent comprises injecting analytical reagent using a syringe pump.

13. The method according to claim 1, further comprising the spectral analysis being an optical spectral analysis, and establishing the baseline analysis being measuring baseline optical density values of the formation fluid for at least one wavelength prior to mixing the analytical reagent, then storing the baseline optical density values with a memory means.

14. The method according to claim 1, wherein an extractor pump extracts formation fluid from a stopped flowline so as to induce analytical reagent injection into the flowline.

15. The method according to claim 14, wherein injecting analytical reagent comprises injecting a predetermined volume of analytical reagent.

16. The method according to claim 15, wherein injecting the predetermined volume of the reagent comprises setting an extraction pump rate.

17. The method according to claim 15, wherein injecting the predetermined volume of the reagent comprises setting an extraction time.

18. The method according to claim 14, wherein the extractor pump is a syringe piston.

19. The method according to claim 14, wherein extracting formation fluid comprises using a flow-line pump.

20. The method according to claim 14, wherein extracting formation fluid comprises using a step piston.

21. The method according to claim 20, wherein extracting formation fluid comprises adjusting metering valve settings.

22. The method according to claim 1, wherein storing analytical reagent comprises storing different reagents in first and auxiliary reagent containers.

23. The method according to claim 1, wherein the result of the formation fluid baseline analysis indicates if the stored analytical reagent is to be used.

* * * * *

UNITED STATES PATENT AND TRADEMARK OFFICE
CERTIFICATE OF CORRECTION

PATENT NO. : 7,427,504 B2
APPLICATION NO. : 10/667639
DATED : September 23, 2008
INVENTOR(S) : Torleif Torgersen et al.

It is certified that error appears in the above-identified patent and that said Letters Patent is hereby corrected as shown below:

On the Title page item (73), should read:
Assignee: Schlumberger Technology Corporation (Ridgefield, CT)

Signed and Sealed this

Sixteenth Day of November, 2010

David J. Kappos
*Director of the United States Patent and Trademark Office*